United States Patent
Bollinger et al.

(10) Patent No.: US 8,258,128 B2
(45) Date of Patent: Sep. 4, 2012

(54) ORGANIC COMPOUNDS

(75) Inventors: Pietro Bollinger, Bottmingen (CH); Mahavir Prashad, Montville, NJ (US); Bernhard Riss, Hunigue (FR); Janet Dawson King, Bennwil (CH); Peter C. Hiestand, Allschwil (CH); Yugang Liu, Bridgewater, NJ (US); Jonathan King, Bennwil (CH); Vincent Schmid, Domdidier (CH); Friedrich Schuerch, Frenkendorf (CH)

(73) Assignee: Novartis AG, Basel (CH)

( * ) Notice: Subject to any disclaimer, the term of this patent is extended or adjusted under 35 U.S.C. 154(b) by 855 days.

(21) Appl. No.: 12/224,734

(22) PCT Filed: Feb. 21, 2007

(86) PCT No.: PCT/EP2007/001507
§ 371 (c)(1),
(2), (4) Date: Dec. 12, 2008

(87) PCT Pub. No.: WO2007/096150
PCT Pub. Date: Aug. 30, 2007

(65) Prior Publication Data
US 2009/0131408 A1 May 21, 2009

(30) Foreign Application Priority Data
Feb. 23, 2006 (EP) .................................. 06003702

(51) Int. Cl.
*A61K 31/33* (2006.01)
*A61K 31/55* (2006.01)
*A61K 31/38* (2006.01)
*A01N 43/00* (2006.01)
*A01N 43/12* (2006.01)

(52) U.S. Cl. ............ 514/213.01; 514/215; 514/217; 514/438; 514/443

(58) Field of Classification Search .................. None
See application file for complete search history.

(56) References Cited

U.S. PATENT DOCUMENTS

| 4,745,111 A | 5/1988 | Steiner et al. | |
| 4,971,964 A * | 11/1990 | Suzuki et al. | ............ 514/215 |

FOREIGN PATENT DOCUMENTS

| DE | 2257443 | 11/1972 |
| WO | WO00/64904 | 11/2000 |
| WO | WO00/73313 A1 | 12/2000 |
| WO | PCT/EP2007/001507 | 2/2007 |

OTHER PUBLICATIONS

Bohm et al. "Scaffold hopping", DrugDisc.TodayTech., 2004, vol. 1, issue 3, pp. 217-224.*
Silverman, The Organic Chemistry of Drug Design and Drug Action, 2nd ed., 2004, pp. 25-34.*
Patani et al. "Bioisosterism: A Rational Approach in Drug Design", Chem.Rev., 1996, vol. 96, pp. 3147-3176.*

* cited by examiner

*Primary Examiner* — Jeffrey S. Lundgren
*Assistant Examiner* — Stephanie Springer
(74) *Attorney, Agent, or Firm* — Ann R. Pokalsky, Esq.; Dilworth & Barrese, LLP

(57) ABSTRACT

The present invention relates to novel aza-thia-benzoazulene derivatives of formula I as defined in the claims, their preparation, the use of these novel compounds for the preparation of pharmaceutical compositions, the use of these novel compounds and compositions for managing arthritis and arthritis-related conditions as well as in the treatment of pain in animals and humans. More particularly, the present invention relates to pharmaceutical, preferably veterinary compositions and methods for reducing inflammation and pain associated with acute inflammation of body parts, particularly joints, due to injury or due to arthritic conditions or other disease conditions.

15 Claims, No Drawings

ORGANIC COMPOUNDS

This application is a U.S. National Stage application of International Application No. PCT/EP2007/001507 filed Feb. 21, 2007, which claims the benefit of European Application No. EP 06003702.5, filed Feb. 23, 2006, the entire contents of both are hereby incorporated herein by reference.

TECHNICAL FIELD

The present invention relates to novel aza-thia-benzoazulene derivatives of formula I, their preparation, the use of these novel compounds for the preparation of pharmaceutical compositions, the use of these novel compounds and compositions for managing arthritis and arthritis-related conditions as well as in the treatment of pain in animals and humans. More particularly, the present invention relates to pharmaceutical, preferably veterinary compositions and methods for reducing inflammation and pain associated with acute or chronic inflammation of body parts, particularly joints, due to injury or due to arthritic conditions or other disease conditions.

Domestic animals, as human beings suffer pain in response to a number of stimuli such as: inflammatory and degenerative processes as well as trauma and surgery. Pain has a protective function, resulting in avoidance of potentially dangerous circumstances and allowing healing processes to take place. Total ablation of pain responses is not a desirable goal however there is a very real need to control pain in domestic animals as well as in man, for humane and ethical reasons and for economic reasons as well. The humane and ethical reasons should be self evident. On the economic front, animals suffering from low grade pain or discomfort do not perform their best, be this a racing horse or a production animal such as a pig or ruminant. Osteoarthritis is a disease of particular importance in dogs, cats and horses. The causes of this disease are complex and involve conformational and ageing factors, that cause increased wear and tear on joints, as well as degenerative processes such as hip and elbow dysplasia and osteochondrosis dissecans. The causes of these conditions are a complex mixture of genetic, nutritional and management factors. Osteoarthritis results in considerable low grade chronic pain in dogs and cats as it does in human beings. Another, rarer cause of sustained severe arthritic pain is the autoimmune disease, rheumatoid arthritis. This disease has been described in domestic species but it is not encountered with anything approaching the frequency of osteoarthritis. In addition to the pain encountered in these diseases, they also have a significant degenerative component. Inflammatory processes within the joint structure result in the release of a multiplicity of pro-inflammatory mediators such as the cytokines interleukin 1 and tumor necrosis factor, and matrix metalloproteinases (MMP) and other proteinases. These factors perpetuate the degeneration and inflammation. The end result is a vicious circle of events that leads to relentless progressive disease.

Arthritis is a general term for abnormal changes in a joint. Arthritis can arise from joint tissue destruction subsequent to an infection, from congenital defects affecting structural architecture, and from stress and trauma to joint surfaces and supporting structures. It is assumed that disorders of the immune system can lead to joint tissue inflammation and degeneration. In commonly seen cases of hip dysplasia, arthritis is partly due to abnormal conformation and misaligned stress points of the coxofemoral joint. The cartilage is adversely impacted and wears away faster than it can regenerate. The bony layer beneath the cushioning cartilage can be exposed and becomes inflamed; the joint capsule surrounding the joint becomes thickened, less elastic and highly sensitive. Blood vessels to and from the area of the joint dilate and the joint becomes swollen and inflamed. Elastic tissues of the joint stiffen, calcium deposits can build up and nerve endings send pain signals to the brain. Motion becomes more and more restricted due to the joint degeneration, and the discomfort and pain prompts the patient to reduce the use of the joint. Unfortunately, the reduced use further compounds the problems associated with arthritis because the patient then gains weight and continued disuse further limits joint mobility.

Considering the complexity of symptoms related to different kinds of arthritis and inflammatory disease, still a need for compositions remains which include analgesic and anti-inflammatory components, as well as components to protect against the abrasion of connective tissue and to support its production. Considering different side effects of current treatments, also a need for compositions remains to avoid side effects like dyspepsia, ulcer and gastrointestinal bleeding and designed for both, short-term and long-term treatment.

The most frequently occurring inflammatory diseases of the musculoskeletal system are: arthritis (osteoarthritis and rheumatoid arthritis in humans and domestic animals) and navicular bone disease which occurs mainly in horses.

Arthritis is a disease that affects the joints. There are several forms, but the most common are osteoarthritis and rheumatoid arthritis. All forms of arthritis occur in humans and non-human animals. Moreover, there are many common minor pains, which are not arthritis but are due to injury, strain or inflammation of tendons and ligaments and are referred to as Soft Tissue Rheumatism.

Soft Tissue Rheumatism: The name refers to aches or pains which arise from structures surrounding the joint such as tendons, muscles, bursae and ligaments. This disease complex may result from mechanical factors such as overuse or misuse of these structures or as a feature of an arthritis illness. Arthritis refers to inflammation within the joint which results in pain, swelling, and warmth around the joint and is often accompanied by difficulty in using the joint. Arthritis may lead to damage within the joint. This damage may be localized when pain is felt in one region or generalized when pain is felt either all over or in many parts of the body. Soft Tissue Rheumatism occurs not only in humans but is also a severe problem in the aging population of pets like cats but especially dogs. Diagnosing this disease in animals is more difficult than in humans where one can observe, for example the following common areas of localized Soft Tissue Rheumatism:

Trigger finger: pain is felt along finger affected which sometimes has a feeling of snapping when extended—brought on by prolonged use of the hands.

D'Quervains tenosynovitis: pain is felt along the outside of the thumb and along the wrist—often seen in mothers with young babies.

Tennis elbow: pain is felt along the outside of the elbow brought on by strenuous activities involving the outstretched arm.

Tendonitis around the shoulder: pain is brought on at certain points of movements particularly while lifting up the arm or reaching for the back.

Trochanteric Bursitis: pain is felt on the outside of the hip joint and along the thigh due to inflammation of a bursa outside the hip.

Bursitis around the knee: There are several bursae around the knee joint which can get inflamed due to pressure i.e. with prolonged kneeling or in association with Arthritis.

Heel pain: can result from inflammation of the Achilles tendon or the tissue under the heel. Both result in pain and stiffness upon initiating walking and pain upon prolonged standing or climbing.

Forefoot: Bunions may give rise to pain on the sides of the forefoot.

Danger signs in soft tissue rheumatism are for example: The joint is red; hot, swollen, painful and difficult to move; muscles get smaller; bone appear crooked; rashes appear, lymph nodes enlarge; fever and chills develop, and there is loss of weight.

Osteoarthritis (OA) is a common disease that develops when linings of joints fail to maintain normal structure, leading to pain and decreased mobility. It is associated with aging and injury (it used to be called "wear-and-tear" arthritis), and can occur secondary to many other conditions. However, in most cases its true cause remains unknown. It is a degenerative disease that most often affects the fingers, neck, lower back, hips, knees, and other joints. It is more common with age and in cases of injury to the joint, overuse of joints and with excess weight. For example, in USA over 20 million individuals have osteoarthritis. Over 50% of people develop this condition by the age of 65.

Osteoarthritis is a common disease not only in men but also well known in dogs. It is the most common cause of chronic pain in dogs and approximately 1 of 5 adult dogs are unable to jump, climb stairs, etc. due to arthritic pain. Many cases of osteoarthritis arise from development errors suffered in puppyhood. Trauma to joints could also be the precursor of degenerative joint changes later in life. This chronic progressive disease is characterized by articular cartilage degeneration and destruction and by alterations in subchondral bone and synovial fluid. Current therapies with non-steroidal anti-inflammatory drugs and agents such as hyaluronic acid do not appear to have significant effects in slowing the progression of the disease. Osteoarthritis is often seen in older cats but can also be seen in young to middle aged cats if the animal has had significant disease or some type of trauma to the joints.

Rheumatoid arthritis affects over 2 million people, more than 60% of them are women. Anyone can get rheumatoid arthritis, including children and the elderly. However, the disease usually begins in the young to middle adult years. Among people with RA, women outnumber men by 3-to-1. In the United States, approximately one percent of the population, or 2.5 million people, have rheumatoid arthritis. It can happen at any age, but usually between the ages of 20 and 45. The characteristic symptoms of inflammatory arthritis are swelling and pain of one and more joints. The affected joints are often warmer than the other joints of the body. Stiffness of the joints when getting up in the morning, or after resting for a time, is very common and is sometimes the first symptom.

Rheumatoid arthritis occurs not only in humans but also frequently in pets. This condition can be seen in cats and dogs of any age. Symptoms to look for: reluctance to walk, reduced motion, limping or favoring one side of the body, lethargic, fever, loss of appetite, obvious pain and discomfort.

Navicular Bone Disease (NBD) is a complicated disease that is a common cause of lameness in horses. The disease results in degenerative changes to the navicular bone, the cartilage and the deep digital flexor tendon. Often the disease is primarily associated with the cartilage and the tendons rather than the bone. NBD has to be treated by elaborate methods but nevertheless almost always results in the loss of the affected, but otherwise healthy, horse. NBD strikes all horse breeds and usually occurs in 6-12-year-old horses. NBD starts insidiously but can be detected without exception already at a stage in which the horse does not show any symptoms yet.

NBD usually occurs only in the horse's front feet, is most common in middle to heavyweight hunter types, particularly those that are kept as hacks rather than racehorses or showjumpers and is extremely rare in ponies. Factors that could be influential here are the weight of the horse in proportion to the size of his hoof and also protection against navicular may be gained from the long, slow fitness work that competition animals undergo and grazing ponies do naturally.

The patho-physiology of NBD is not at all clear. Among the numerous theories regarding its etiology, two are of preeminent interest: Bad blood circulation in the foot is blamed on the one hand and changes in the biomechanical properties of the foot, i.e. the navicular bone, of the horses are blamed on the other hand. Correspondingly, there are primarily two methods of treatment, which are often employed: The biomechanical explanation of the disease calls for corresponding measures of the farrier as well as for chirurgical methods. The blood circulation theory, on the other hand, rather indicates drug treatment of the horse that aims at improving the blood circulation in the navicular bone but also in the surrounding tissue. Attempts have therefore been made to achieve an improvement using anticoagulants, e.g. warfarin. The inflammation of the affected bone is also treated with steroidal and non-steroidal anti-inflammatory drugs. However, these methods are only partly successful, their efficiency is difficult to assess, they are elaborate and, in particular, they do not achieve a permanent cure of the disease. Accordingly, there is still an urgent need to solve the problem.

Since up to now no reliable models for NBD exist, the inventive veterinary compositions have to be tested in horses suffering from this disease.

Besides of NBD, all the diseases listed above do not occur only in human beings but are observed as well in animals. The older animals become the higher is the risk that they will suffer from one or more of these disease. Especially the population of pets becomes older and older, and there is a real need that the disease is diagnosed early and treated adequately.

All of these conditions and affections are the subject of continuing research looking for better treatments combining pain relief and disease modification by avoiding side-effects, as damaging stomach and intestinal mucous.

Pain and inflammation are also features of other conditions affecting domestic animal species, notably in infectious diseases, post trauma and post surgery and this pain also requires treatment.

Currently the drugs available for pain management and pain relief fall into two main categories. First there are the opiates and the opiate derivatives. These are powerful analgesics but tend to have a rather short duration of action and they have a number of undesirable side effects such as somnolence and constipation. A further consideration in considering opiates is that they offer many opportunities for abuse and as such are unsuited for use in ambulatory practice. The second group of analgesics commonly used are the non steroidal anti inflammatory drugs (NSAIDS) best represented by cyclooxygenase (COX) inhibitors. These drugs inhibit prostaglandin and other eicosanoid production by inhibition of the COX enzyme. The first generation COX inhibitors such as ibuprofen and diclofenac have in some cases marked and very serious gastrointestinal and renal side effects. The gastrointestinal effects are particularly marked in dogs and cats and can be fatal. This makes them unattractive for veterinary use and certainly they cannot be used in chronic conditions such as osteoarthritis. Newer drugs that inhibit COX 2 selectively go some way toward alleviating this problem in that they inhibit the COX that is induced in inflammatory processes and spare the COX 1 that is constitutively expressed in the gastrointestinal tract and that has protective function. However, as is known from recent data on these drugs in man that there are nonetheless gastrointestinal consequences of the use of these drugs. It is reasonable to expect the same sort of problems will be manifest in dogs and cats.

For all these reasons there is a long felt need for analgesics with a new mode of action to permit relief of pain in many different animal species but also in humans with particular emphasis on long term use, especially in pets like dogs and cats. The compounds of the present invention are neither opiates nor COX inhibitors and will meet this need. They are much better tolerated by animals, especially cats and dogs, than COX inhibitors.

Additionally arthritis is a chronic progressive degenerative disease as we have described hereinabove. Drugs affecting the mediators involved in this process could have a direct effect on the pathological process involved and slow down or even arrest the progress of the disease. This invention can act in such a manner in addition to its analgesic effects.

This could be an effect of the invention itself or it could be in combination with another agent such as polysulfated glycosaminoglycan (PSGAG) or nutraceutical preparations such as Glucosamine.

DISCLOSURE OF THE INVENTION

The present invention is based on the synthesis of a new class of compounds, i.e. aza-thia-benzoazulene derivatives of formula I as defined herein below, that show a beneficial effect in the prophylaxis and therapy of a broad range of inflammatory diseases. It has now surprisingly been found that the administration of a compound of the formula I or a pharmaceutical composition containing as active ingredient a compound of the formula I to a human or a non-human animal suffering from one or more of the above-referenced diseases results in a significant and sustained improvement of the quality of life and a significant reduction of pain caused by the disease. With radiographic studies it should be possible to show that the inventive compounds and compositions do not only show a beneficial effect on the symptoms but actually act as a disease modifier, i.e. exhibit a real curative effect. Surprising is also the beneficial effect of the inventive composition on navicular bone disease (NBD) in horses. A particularly important advantage of the inventive compounds and pharmaceutical compositions containing such a compound is their pronounced efficacy and ability of long-term use without causing adverse effects in the treated human or animal, especially in dogs. The pharmaceutical compositions according to this invention have a very positive influence on the formation of bones and cartilage. Unexpectedly, these compositions do not show the undesired side effects in pets, especially in dogs that are observed after treatment with NSAIDs, as for example diclofenac.

In principle, human and non-human animals can be the target for this kind of treatment. The expression non-human animals includes farm animals, such as cows, pigs, sheep and goats, poultry, such as hens, turkeys and geese, animals bred for their fur, such as mink, foxes, chinchillas, rabbits and the like, as well as domestic animals and pets, such as cats and dogs. Most preferred target animals are pets like dogs and cats, especially dogs suffering from one or more diseases described herein before. One important target group consists of aging pets, especially older cats and dogs, preferably old dogs. Another preferred target group consists of hoofed animals, including wild and domesticated animals like antelope, camels, cattle, deer and elk, donkeys, giraffes, goats, llamas and alpacas, hippos, horses, moose, okapis, pigs, rhinos, unicorns, warthogs, and zebras but especially cattle and horse, and meat producing animals used for breeding, especially pigs. Other non-human animals are of course not excluded.

The active ingredients of the formula I are novel compounds and can be prepared in accordance with the preparation process described herein below.

Administration routes, dose and dosage frequency: It is envisioned that the present invention will be administered by systemic or non-systemic pathways, preferably systemically e.g. orally, topically (transdermally, transmucosally) or in form of suppository, subcutaneous, intramuscular, intravenous or via intra articular routes. The preferred route of administration is orally, subcutaneously and intramuscularly. Most preferred is the oral uptake. The recommended daily dosage for the compounds of the formula I is a therapeutically effective amount that depends on the bodyweight of the human or animal that has to be treated and the severity of the symptoms. In general the therapeutically effective amount is for most humans and animals from about 0.01 to about 500 mg/kg/day, preferably 0.01 to about 300 mg/kg/day, more preferably from about 0.1 to about 100 mg/kg/day. The compound of the present invention will be dosed at a frequency varying from several times daily, once daily, once every second day to once weekly. With special depot formulations one might reduce the frequency of treatment to once monthly or every three months.

It can be advantageous to add to the inventive composition a biologically effective amount of natural products that have a beneficial impact on inflammatory conditions. Examples of such beneficial natural compounds are standardized extracts of White Willow Bark, Green-lipped Mussel, Boswellic Acid, glucosamine, and chondroitin sulfate.

In view of the above, the present invention seeks to realize the following objects and advantages:

It is a primary objective of the present invention to provide a novel aza-thia-benzoazulene compounds of formula I

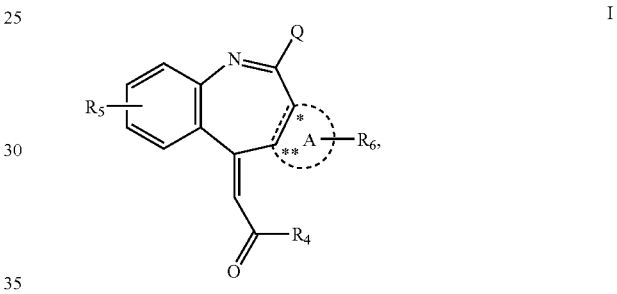

wherein

Q is $-N(R_1)(R_2)$ or $-O-R_3$;

$R_1$ and $R_2$ independently of each other is H, $C_1$-$C_6$-alkyl, $C_1$-$C_6$-alkylcarbonyl, $C_2$-$C_6$-alkenyl, $C_3$-$C_6$-cycloalkyl, $C_3$-$C_6$-cycloalkylcarbonyl, $C_1$-$C_6$-alkoxy-$C_1$-$C_6$-alkyl, di($C_1$-$C_6$-alkyl)amino-$C_1$-$C_6$-alkyl, $C_1$-$C_6$-alkyl-carboxy-$C_1$-$C_6$-alkyl, amino-$C_1$-$C_6$-alkyl, $C_1$-$C_6$-hydroxyalkyl, $C_1$-$C_6$-alkylamino-$C_1$-$C_6$-alkyl or $R_1$ and $R_2$ form together with the nitrogen atom to which they are attached a ring containing 2 to 5 carbon atoms and optionally one additional nitrogen, sulphur or oxygen atom, said ring optionally being substituted with 1 to 4 substituents selected from the group consisting of $C_1$-$C_4$-alkyl and $C_1$-$C_4$-alkoxy;

$R_3$ is $C_1$-$C_6$-alkyl, $C_1$-$C_6$-alkylcarbonyl, $C_2$-$C_6$-alkenyl, $C_3$-$C_6$-cycloalkyl, $C_3$-$C_6$-cycloalkylcarbonyl, $C_1$-$C_6$-alkoxy-$C_1$-$C_6$-alkyl, di($C_1$-$C_6$-alkyl)amino-$C_1$-$C_6$-alkyl, $C_1$-$C_6$-carboxy-$C_1$-$C_6$-alkyl, amino-$C_1$-$C_6$-alkyl, $C_1$-$C_6$-hydroxyalkyl, $C_1$-$C_6$-alkylamino-$C_1$-$C_6$-alkyl;

$R_4$ is OH, $NH_2$, $C_1$-$C_6$-alkyloxy, $C_1$-$C_6$-alkylamino, di($C_1$-$C_6$-alkyl)amino, amino($C_1$-$C_6$-alkyl)amino, $C_1$-$C_6$-alkylthio, unsubstituted or one to five fold substituted aryloxy, unsubstituted or one to five fold substituted arylamino, the substituents independently from each other being selected from the group consisting of halogen, nitro, cyano, $C_1$-$C_6$-alkyl, halo-$C_1$-$C_6$-alkyl, $C_1$-$C_6$-alkoxy, halo-$C_1$-$C_6$-alkoxy, $C_2$-$C_6$-alkenyl, halo-$C_2$-$C_6$-alkenyl, $C_2$-$C_6$-alkinyl, $C_3$-$C_6$-cycloalkyl, $C_2$-$C_6$-alkenyloxy, halo-$C_2$-$C_6$-alkenyloxy, $C_1$-$C_6$-alkylthio, halo-$C_1$-$C_6$-alkylthio, $C_1$-$C_6$-alkylsulfonyloxy, halo-$C_1$-$C_6$-alkylsulfonyloxy, $C_1$-$C_6$-alkylsulfinyl, halo-$C_1$-$C_6$-alkylsulfinyl, $C_1$-$C_6$-alkylsulfonyl, halo-$C_1$-$C_6$-alkylsulfonyl, $C_2$-$C_6$-alkenylthio, halo-$C_2$-$C_6$-alkenylthio, $C_2$-$C_6$-alkenylsulfinyl, halo-$C_2$-$C_6$-alkenylsulfinyl, $C_2$-$C_6$-alkenylsulfonyl, halo-$C_2$-$C_6$-alkenylsulfonyl, $C_1$-$C_6$-alkylamino, di-$C_1$-$C_6$-alkylamino, $C_1$-$C_6$-alkylsulfonylamino, halo-$C_1$-$C_6$-alkylsulfonylamino, $C_1$-$C_6$-alkylcarbonyl, halo-$C_1$-$C_6$-alkylcarbonyl and $C_1$-$C_6$-alkoxycarbonyl;

$R_5$ is H, halogen, $NO_2$, CN, $NH_2$, SH, OH, $CO_2H$, CHO, $C_1$-$C_6$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_1$-$C_6$-alkylcarboxy, $C_1$-$C_6$-alkylcarbonyl, aminocarbonyl, $C_1$-$C_6$-alkylcarbonylamino, $C_1$-$C_6$-alkylcarbonyloxy or $C_1$-$C_6$-alkylsulfonylamino;

$R_6$ is H, halogen, $NO_2$, CN or $C_1$-$C_6$-alkyl; and
the ring system

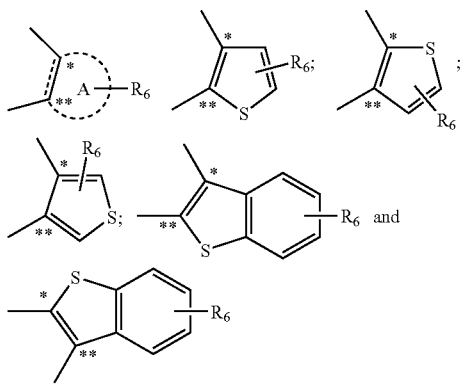

is selected from the group consisting of
and a physiologically acceptable ester or a pharmaceutically acceptable salt thereof.

By the term "physiologically acceptable ester" as applied to the compounds of the invention, e.g. the compounds of formula I, is meant esters in which the carboxylic group is esterified and which are hydrolysable under physiological conditions to yield an alcohol which is itself physiologically acceptable, e.g. non-toxic at desired dosage levels. Such esters include e.g. esters with aliphatic alcohols having 1 to 4 carbon atoms.

The compounds of formula I can form salts, for example acid addition salts. These are formed for example with strong inorganic acids, typically mineral acids, e.g. sulfuric acid, a phosphoric acid or a halogen acid, or with strong organic carbonic acids, typically $C_1$-$C_4$-alkanecarbonic acids substituted where appropriate for example by halogen, e.g. acetic acid, such as dicarbonic acids that are unsaturated where necessary, e.g. oxalic, malonic, maleic, fumaric or phthalic acid, typically hydroxycarbonic acids, e.g. ascorbic, lactic, malic, tartaric or citric acid, or benzoic acid, or with organic sulfonic acids, typically $C_1$-$C_4$alkane or arylsulfonic acids substituted where appropriate for example by halogen, e.g. methane-sulfonic or p-toluenesulfonic acid. In a broader sense, compounds of formula I with at least one acid group can form salts with bases. Suitable salts with bases are for example metal salts, typically alkali or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl, diethyl, triethyl or dimethylpropylamine, or a mono-, di- or trihydroxy-lower alkylamine, e.g. mono-, di- or triethanolamine. Furthermore, where appropriate corresponding internal salts may also be formed. The free form is preferred. Among the salts of compounds of formula I, the hydrochemically beneficial salts are preferred. Hereinbefore and hereinafter, the free compounds of formula I and their salts are understood where appropriate to include also by analogy the corresponding salts or free compounds of formula I. The same applies for the pure enantiomers of formula I and salts thereof.

A preferred subgroup of compounds within the formula I consists compounds wherein the ring system

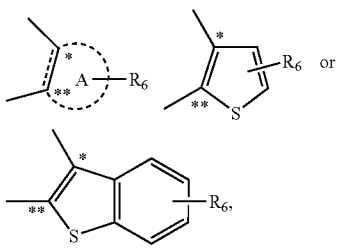

is selected from the group consisting of
most preferably

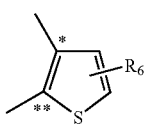

and R6 is as defined under formula I.

Another preferred subgroup of compounds within the formula I consist of compounds of the formula Ia

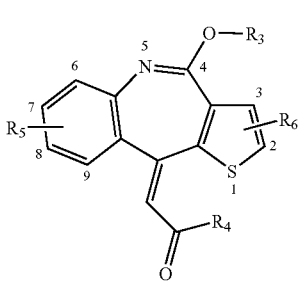

(Ia)

wherein $R_3$, $R_4$ and $R_5$ are defined as under formula I or stand preferably for $R_3$ is $C_1$-$C_6$-alkyl, most preferably methyl or ethyl;
$R_4$ is OH, $NH_2$, or $C_1$-$C_6$-alkyloxy, most preferably OH, methoxy or ethoxy; and
$R_5$ is H, or halogen, most preferably H, F, or Cl. This group is exemplified in table 1.

A preferred embodiment within the compounds of the formula Ia is any individual compound selected from the group consisting of [7-Chloro-10-hydroxy-3-thia-9-aza-benzo[f]azulen-4-ylidene]-acetic acid; [7-Chloro-10-methoxy-3-thia-9-aza-benzo[f]azulen-4-ylidene]-acetic acid; [7-Chloro-10-ethoxy-3-thia-9-aza-benzo[f]azulen-4-ylidene]-acetic acid; [2-Chloro-10-hydroxy-3-thia-9-aza-benzo[f]azulen-4-ylidene]-acetic acid; [2-Chloro-10-methoxy-3-thia-9-aza-benzo[f]azulen-4-ylidene]-acetic acid; [2-Chloro-10-ethoxy-3-thia-9-aza-benzo[f]azulen-4-ylidene]-acetic acid; [2-Chloro-7-fluoro-10-hydroxy-3-thia-9-aza-benzo[f]azulen-4-ylidene]-acetic acid; [2-Chloro-7-fluoro-10-methoxy- 3-thia-9-aza-benzo[f]azulen-4-ylidene]-acetic acid; [2-Chloro-7-fluoro-10-ethoxy-3-thia-9-aza-benzo[f]azulen-4-ylidene]-acetic acid; [2,7-Difluoro-10-hydroxy-3-thia-9-aza-benzo[f]azulen-4-ylidene]-acetic acid; [2,7-Difluoro-10-methoxy-3-thia-9-aza-benzo[f]azulen-4-ylidene]-acetic acid; [2,7-Difluoro-10-ethoxy-3-thia-9-aza-benzo[f]azulen-4-ylidene]-acetic acid; [2,7-Dichloro-10-hydroxy-3-thia-9-aza-benzo[q]azulen-4-ylidene]-acetic acid; [2,7-Dichloro-10-ethoxy-3-thia-9-aza-benzo[f]azulen-4-ylidene]-acetic acid; and [2,7-Dichloro-10-methoxy-3-thia-9-aza-benzo[f]azulen-4-ylidene]-acetic acid.

The most preferred compound within the compounds of the formula Ia is [2,7-Dichloro-10-methoxy-3-thia-9-aza-benzo[f]azulen-4-ylidene]-acetic acid, and especially the cis isomer [2,7-Dichloro-10-methoxy-3-thia-9-aza-benzo[f]azulen-4-ylidene]-acetic acid.

An interesting subgroup of compounds within the formula I consist of compounds of the formula Ib

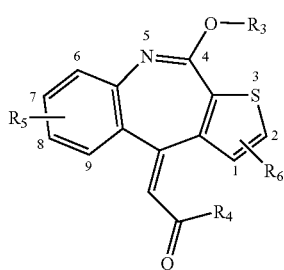

(Ib)

wherein $R_3$, $R_4$ and $R_5$ are defined as under formula I. This group is exemplified in table 2. Another further interesting subgroup of compounds within the formula I consist of compounds of the formula Ic

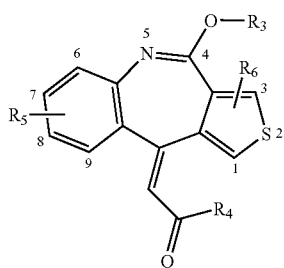

(Ic)

wherein $R_3$, $R_4$ and $R_5$ are defined as under formula I. This group is exemplified in table 3. Another preferred subgroup of compounds within the formula I consist of compounds of the formula Id

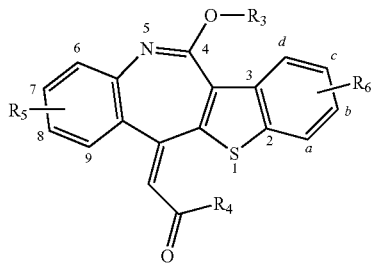

(Id)

wherein $R_3$, $R_4$ and $R_5$ are defined as under formula I. Group Id is exemplified in table 4.

Within all given chemical formula the substituents have the following meanings:

Alkyl—as a group per se and as structural element of other groups and compounds such as halogen-alkyl, alkylamino, alkoxy, alkylthio, alkylsulfinyl and alkylsulfonyl—is, in each case with due consideration of the specific number of carbon atoms in the group or compound in question, either straight-chained, i.e. methyl, ethyl, propyl, butyl, pentyl, hexyl, heptyl or octyl, or branched, e.g. isopropyl, isobutyl, sec.-butyl, tert.-butyl, isopentyl, neopentyl or isohexyl.

Cycloalkyl—as a group per se and as structural element of other groups and compounds such as halocycloalkyl, cycloalkoxy and cycloalkylthio,—is, in each case with due consideration of the specific number of carbon atoms in the group or compound in question, cyclopropyl, cyclobutyl, cyclopentyl, cyclohexyl, cycloheptyl or cyclooctyl.

Alkenyl—as a group per se and as structural element of other groups and compounds—is, in each case with due consideration of the specific number of carbon atoms in the group or compound in question and of the conjugated or isolated double bonds—either straight-chained, e.g. allyl, 2-butenyl, 3-pentenyl, 1-hexenyl, 1-heptenyl, 1,3-hexadienyl or 1,3-octadienyl, or branched, e.g. isopropenyl, isobutenyl, isoprenyl, tert.-pentenyl, isohexenyl, isoheptenyl or isooctenyl.

Alkinyl—as a group per se and as structural element of other groups and compounds—is, in each case with due consideration of the specific number of carbon atoms in the group or compound in question and of the conjugated or isolated double bonds—either straight-chained, e.g. propargyl, 2-butinyl, 3-pentinyl, 1-hexinyl, 1-heptinyl, 3-hexen-1-inyl or 1,5-heptadien-3-inyl, or branched, e.g. 3-methylbut-1-inyl, 4-ethylpent-1-inyl, 4-methylhex-2-inyl or 2-methylhept-3-inyl.

Aryl is phenyl or naphthyl.

As a rule, halogen signifies fluorine, chlorine, bromine or iodine. The same applies to halogen in combination with other significances, such as halogenalkyl. Most preferred halogen is chlorine.

Halogen-substituted carbon-containing groups and compounds may be partially halogenated or perhalogenated, whereby in the case of multiple halogenation, the halogen substituents may be identical or different. Examples of halogen-alkyl—as a group per se and as structural element of other groups and compounds such as halogen-alkoxy or halogen-alkylthio,—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers substituted once to eleven times by fluorine, chlorine and/or bromine, such as $CF(CF_3)(CHF)_2CF_3$ or $CH_2(CF_2)_3CF_3$; and hexyl or one of its isomers substituted once to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Alkoxy groups preferably have a chain length of 1 to 6 carbon atoms. Alkoxy is for example methoxy, ethoxy, propoxy, isopropoxy, n-butoxy, isobutoxy, sec.-butoxy and tert.-butoxy, as well as the isomers pentyloxy and hexyloxy; preferably methoxy and ethoxy. Halogenalkoxy groups preferably have a chain length of 1 to 6 carbon atoms. Halogenalkoxy is e.g. fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

An example for $C_1$-$C_6$-alkylcarbonyl is $CH_3$—C(O)—, for $C_3$-$C_6$-cycloalkylcarbonyl is cyclopropyl-C(O)—, for $C_1$-$C_6$-alkoxy-$C_1$-$C_6$-alkyl is $CH_3$—O—$CH_2$—, for di($C_1$-$C_6$-alkyl) amino-$C_1$-$C_6$-alkyl is $(CH_3)(C_2H_5)$N—$CH_2CH_2$—, for $C_1$-$C_6$-alkyl-carboxy-$C_1$-$C_6$-alkyl is $CH_3$—O—C(O)—$CH_2$—, for amino-$C_1$-$C_6$-alkyl is $H_2$N—$CH_2CH_2$—, for $C_1$-$C_6$-hydroxyalkyl is HO—CH2- or $CH_3$—CH(OH)—$CH_2$—, for $C_1$-$C_6$-alkylamino-$C_1$-$C_6$-alkyl is CH3(H)N—$CH_2CH_2$—.

The compounds of the formula I, exist in both cis and trans isomeric forms, i.e. as Z and E isomers. The present invention is to be understood as embracing both the individual cis and trans isomers as well as mixtures thereof. In the present specification and claims cis (Z) and trans (E) isomers are designated in accordance with conventional CIP-nomenclature [Angew. Chem. 94, 614 (1982) and Loc. cit.]. Thus the cis isomer is the isomer of formula I' and the trans isomer the isomer of formula I"

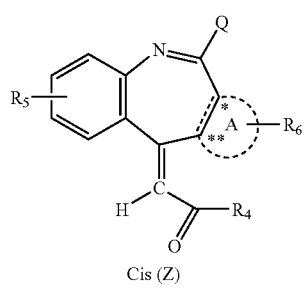

Cis (Z) (I')

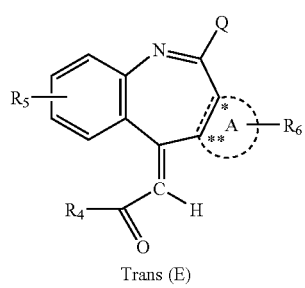

Trans (E) (I")

In general, the cis (Z) isomers are preferred. Accordingly the compounds of the invention are preferably in predominantly cis form. Most preferably they are in pure or substantially pure cis form. Individual cis and trans isomers of compounds of the invention may be obtained in accordance with techniques known in the art, e.g. by separation of cis/trans isomer mixtures, e.g. chromatographically.

The compounds of the formula I can be prepared as summarized in the following synthesis scheme and explained and exemplified in greater detail hereinafter.

Synthesis scheme:

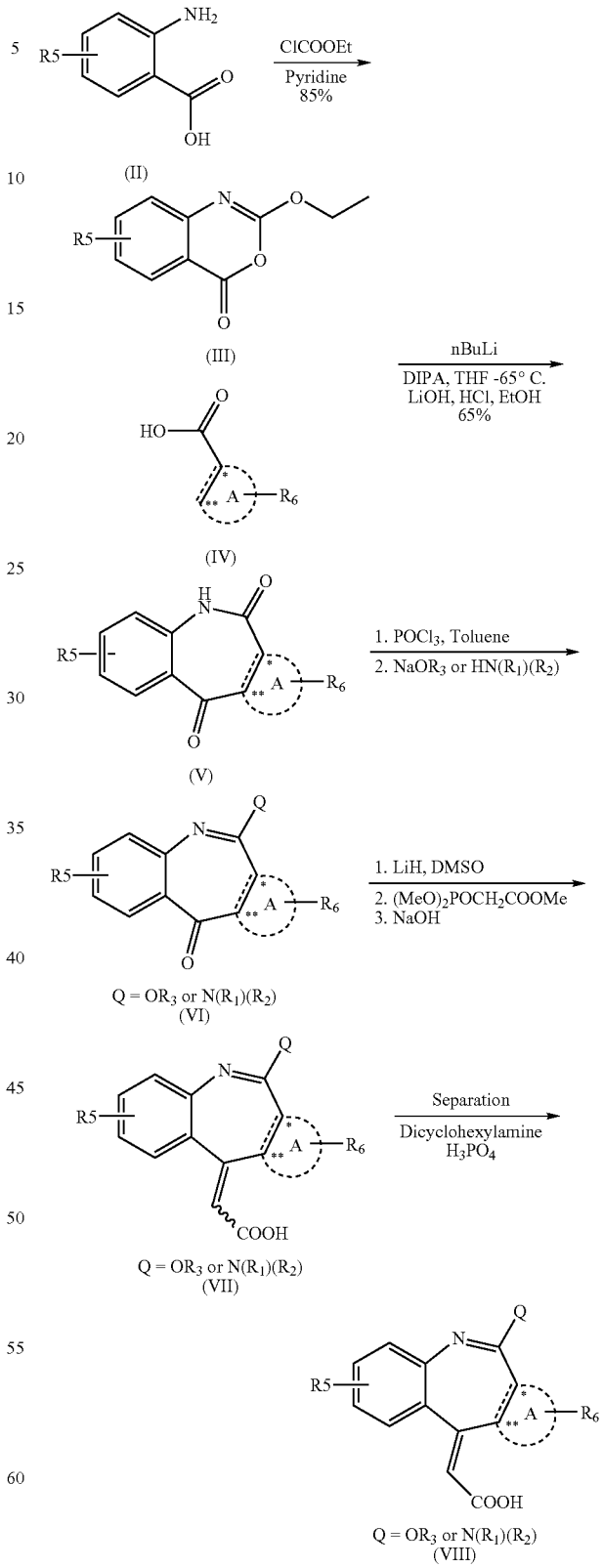

A further object of the invention is the process for the preparation of the compounds of formula I, respectively in free form or in a physiologically acceptable ester form or pharmaceutically acceptable salt form, for example characterized in that a compound of formula

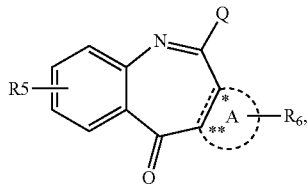

VI which is known or may be produced analogously to corresponding known compounds, and wherein $R_5$, $R_6$, A and Q are defined as given for formula I, is reacted in a Horner-Wittig reaction process with a compound of formula

 (MeO)$_2$POCH$_2$COOMe                    IX, which is known or may be prepared analogously to corresponding known compounds, optionally in the presence of a basic catalyst, the resulting racemic ester optionally saponified in the presence of a basic catalyst and the desired isomer isolated, optionally in the presence of an amine, from the resulting isomeric mixture, and if desired, a compound of formula I obtainable according to the method or in another way, respectively in free form or in salt form, is converted into another compound of formula I, a mixture of isomers obtainable according to the method is separated and the desired isomer isolated and/or a free compound of formula I obtainable according to the method is converted into a salt or a salt of an compound of formula I obtainable according to the method is converted into the free compound of formula I or into another salt.

What has been stated above for salts of compounds I also applies analogously to salts of the starting materials listed hereinabove and herein below.

The reaction partners can be reacted with one another as they are, i.e. without the addition of a solvent or diluent, e.g. in the melt. In most cases, however, the addition of an inert solvent or diluent, or a mixture thereof, is of advantage. Examples of such solvents or diluents are: aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethylether, dimethoxydiethylether, tetrahydrofuran or dioxane; ketones such as acetone, methyl ethyl ketone or methyl isobutyl ketone; amides such as N,N-dimethylformamide, N,N-diethylformamide, N,N-dimethylacetamide, N-methylpyrrolidone or hexamethylphosphoric acid triamide; nitriles such as acetonitrile or propionitrile; and sulfoxides, such as dimethyl sulfoxide. Preferred solvents are sulfoxides, in particular dimethyl sulfoxide.

Suitable bases for facilitating the reaction are e.g. alkali metal or alkaline earth metal hydroxides, hydrides, amides, alkanolates, acetates, carbonates, dialkylamides or alkylsilylamides; alkylamines, alkylenediamines, optionally N-alkylated, optionally unsaturated, cycloalkylamines, basic heterocycles, ammonium hydroxides, as well as carbocyclic amines. Those which may be mentioned by way of example are sodium hydroxide, hydride, amide, methanolate, acetate, carbonate, potassium tert.-butanolate, hydroxide, carbonate, hydride, lithium diisopropyl amide, potassium bis(trimethylsilyl)-amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide, as well as 1,5-diazabicyclo[5.4.0]undec-5-ene (DBU). Preference is given to alkali metal or alkaline earth metal hydrides, especially to metal hydrides, in particular lithium hydride for the Horner-Wittig process and sodium hydroxide for the saponification of the ester.

The reaction advantageously takes place in a temperature range of ca. 0° C. to ca. 100° C., preferably from ca. 10° C. to ca. 80° C.

In a preferred process, a compound of formula IV is reacted at a temperature of between 30° C. and 60° C. in dimethyl sulfoxide with a compound of formula IX in the presence of lithium hydride.

A still further object of the invention is the process for the preparation of the compounds of formula VI, respectively in free form or in salt form, for example characterized in that a compound of formula

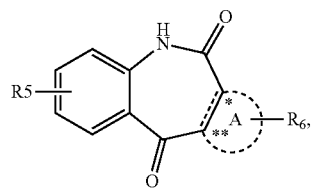

V which is known or may be produced analogously to corresponding known compounds, in which $R_5$, $R_6$, and A are defined as for formula I, is reacted with POCl$_3$ to give an intermediate compound of formula VI, wherein Q is Cl, which is then subsequently, optionally in the presence of a basic catalyst, reacted with HOR$_3$ or HN(R$_1$)(R$_2$), which are known or may be produced analogously to corresponding known compounds and wherein R$_1$, R$_2$, and R3 are defined as for formula I.

The reaction partners can be reacted with one another as they are, i.e. without the addition of a solvent or diluent, e.g. in the melt. In most cases, however, the addition of an inert solvent or diluent, or a mixture thereof, is of advantage. Examples of such solvents or diluents are: aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethylether, dimethoxydiethylether, tetrahydrofuran or dioxane; ketones such as acetone, methyl ethyl ketone or methyl isobutyl ketone; amides such as N,N-dimethylformamide, N,N-diethylformamide, N,N-dimethylacetamide, N-methylpyrrolidone or hexamethylphosphoric acid triamide; nitriles such as acetonitrile or propionitrile; and sulfoxides, such as dimethyl sulfoxide. Preferred solvents are aromatic, aliphatic and alicyclic hydrocarbons, in particular toluene.

The reaction advantageously takes place in a temperature range of ca. −20° C. to ca. 100° C., preferably from ca. −10° C. to ca. 30° C.

In a preferred process, a compound of formula V is reacted at a temperature of between −10° C. and 30° C. in toluene with $POCl_3$ and then subsequently with $NaOR_3$ or $HN(R_1)(R_2)$.

A still further object of the invention is the process for the preparation of the compounds of formula V, for example characterized in that a compound of formula

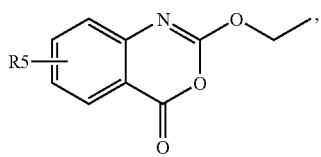

III which is known or may be produced analogously to corresponding known compounds, and wherein $R_5$ is defined as given for formula I, optionally in the presence of a basic catalyst, is reacted with a compound of formula

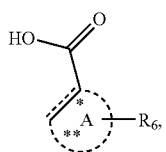

IV which is known or may be produced analogously to corresponding known compounds, and wherein $R_6$ and A are defined as given for formula I.

The reaction partners can be reacted with one another as they are, i.e. without the addition of a solvent or diluent, e.g. in the melt. In most cases, however, the addition of an inert solvent or diluent, or a mixture thereof, is of advantage. Examples of such solvents or diluents are: aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethylether, dimethoxydiethylether, tetrahydrofuran or dioxane; ketones such as acetone, methyl ethyl ketone or methyl isobutyl ketone; amides such as N,N-dimethylformamide, N,N-diethylformamide, N,N-dimethylacetamide, N-methylpyrrolidone or hexamethylphosphoric acid triamide; nitriles such as acetonitrile or propionitrile; and sulfoxides, such as dimethyl sulfoxide. Preferred solvents are ethers, in particular tetrahydrofuran or dioxane.

Suitable bases for facilitating the reaction are e.g. alkali metal or alkaline earth metal hydroxides, hydrides, amides, alkanolates, acetates, carbonates, dialkylamides or alkylsilylamides. Those which may be mentioned by way of example are sodium hydroxide, hydride, amide, methanolate, acetate, carbonate, potassium tert.-butanolate, hydroxide, carbonate, hydride, lithium diisopropyl amide, potassium bis(trimethylsilyl)-amide or calcium hydride. Preference is given to alkali metal or alkaline earth metal hydrides and dialkylamides, especially to metal dialkylamides, in particular lithium diisopropyl amide.

The reaction advantageously takes place in a temperature range of ca. −100° C. to ca. 40° C., preferably from ca. −70° C. to ca. 30° C.

In a preferred process, a compound of formula III is reacted at a temperature of between −65° C. and 20° C. in tetrahydrofuran with a compound of formula IV in the presence of lithium hydride.

In the veterinary area the compounds of formula I according to the invention may be used alone or in combination with other biocides. It may be advantageous to solve with one treatment two or more different problems. Therefore the compounds of the formula I may be combined, for example, with pesticides to expand the activity spectrum. If the range of activity is to be extended to endoparasites, e.g. dewormers, the compounds of formula I are suitably combined with substances having endo-parasitic properties. Of course, they can also be used in combination with antibacterial compositions. The pesticidal combination partners can be adulticides, i.e. compounds that are effective in particular against the adult stage of the target parasites or growth regulators which instead attack the juvenile stages of the parasites. Some combinations may also lead to a synergistic effect, e.g. the total amount of active ingredient can or undesirable side effects be reduced, which is desirable from an ecological and health point of view. Preferred groups of combination partners and especially preferred combination partners are named in the following, whereby combinations may contain one or more of these partners in addition to a compound of formula I.

Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, including repellents or detachers.

Non-limitative examples of suitable insecticides and acaricides are:

| | |
|---|---|
| 1. | Abamectin |
| 2. | AC 303 630 |
| 3. | Acephat |
| 4. | Acrinathrin |
| 5. | Alanycarb |
| 6. | Aldicarb |
| 7. | α-Cypermethrin |
| 8. | Alphamethrin |
| 9. | Amitraz |
| 10. | Avermectin $B_1$ |
| 11. | AZ 60541 |
| 12. | Azinphos A |
| 13. | Azinphos M |
| 14. | Azinphos-methyl |
| 15. | Azocyclotin |
| 16. | *Bacillus subtil.* toxin |
| 17. | Bendiocarb |
| 18. | Benfuracarb |
| 19. | Bensultap |
| 20. | β-Cyfluthrin |
| 21. | Bifenthrin |
| 22. | BPMC |
| 23. | Brofenprox |
| 24. | Bromophos A |
| 25. | Bufencarb |

-continued

| | |
|---|---|
| 26. | Buprofezin |
| 27. | Butocarboxin |
| 28. | Butylpyridaben |
| 29. | Cadusafos |
| 30. | Carbaryl |
| 31. | Carbofuran |
| 32. | Carbophenthion |
| 33. | Cartap |
| 34. | Chloethocarb |
| 35. | Chlorethoxyfos |
| 36. | Chlorfenapyr |
| 37. | Chlorfluazuron |
| 38. | Chlormephos |
| 39. | Chlorpyrifos |
| 40. | Cis-Resmethrin |
| 41. | Clocythrin |
| 42. | Clofentezin |
| 43. | Cyanophos |
| 44. | Cycloprothrin |
| 45. | Cyfluthrin |
| 46. | Cyhexatin |
| 47. | Cyromazine |
| 48. | D 2341 |
| 49. | Deltamethrin |
| 50. | Demeton M |
| 51. | Demeton S |
| 52. | Demeton-S-methyl |
| 53. | Dibutylaminothio |
| 54. | Dichlofenthion |
| 55. | Dicliphos |
| 56. | Diethion |
| 57. | Diflubenzuron |
| 58. | Dimethoat |
| 59. | Dimethylvinphos |
| 60. | Dioxathion |
| 61. | DPX-MP062 |
| 62. | Edifenphos |
| 63. | Emamectin |
| 64. | Endosulfan |
| 65. | Esfenvalerat |
| 66. | Ethiofencarb |
| 67. | Ethion |
| 68. | Ethofenprox |
| 69. | Ethoprophos |
| 70. | Etrimphos |
| 71. | Fenamiphos |
| 72. | Fenazaquin |
| 73. | Fenbutatinoxid |
| 74. | Fenitrothion |
| 75. | Fenobucarb |
| 76. | Fenobucarb |
| 77. | Fenothiocarb |
| 78. | Fenoxycarb |
| 79. | Fenpropathrin |
| 80. | Fenpyrad |
| 81. | Fenpyroximate |
| 82. | Fenthion |
| 83. | Fenvalerate |
| 84. | Fipronil |
| 85. | Fluazinam |
| 86. | Fluazuron |
| 87. | Flucycloxuron |
| 88. | Flucythrinat |
| 89. | Flufenoxuron |
| 90. | Flufenprox |
| 91. | Fonophos |
| 92. | Formothion |
| 93. | Fosthiazat |
| 94. | Fubfenprox |
| 95. | HCH |
| 96. | Heptenophos |
| 97. | Hexaflumuron |
| 98. | Hexythiazox |
| 99. | Hydroprene |
| 100. | Imidacloprid |
| 101. | Insect-active fungi |
| 102. | Insect-active nematodes |
| 103. | Insect-active viruses |
| 104. | Iprobenfos |
| 105. | Isofenphos |

-continued

| | |
|---|---|
| 106. | Isoprocarb |
| 107. | Isoxathion |
| 108. | Ivermectin |
| 109. | λ-Cyhalothrin |
| 110. | Lufenuron |
| 111. | Malathion |
| 112. | Mecarbam |
| 113. | Mesulfenphos |
| 114. | Metaldehyd |
| 115. | Methamidophos |
| 116. | Methiocarb |
| 117. | Methomyl |
| 118. | Methoprene |
| 119. | Metolcarb |
| 120. | Mevinphos |
| 121. | Milbemectin |
| 122. | Moxidectin |
| 123. | Naled |
| 124. | NC 184 |
| 125. | NI-25, Acetamiprid |
| 126. | Nitenpyram |
| 127. | Omethoat |
| 128. | Oxamyl |
| 129. | Oxydemethon M |
| 130. | Oxydeprofos |
| 131. | Parathion |
| 132. | Parathion-methyl |
| 133. | Permethrin |
| 134. | Phenthoat |
| 135. | Phorat |
| 136. | Phosalone |
| 137. | Phosmet |
| 138. | Phoxim |
| 139. | Pirimicarb |
| 140. | Pirimiphos A |
| 141. | Pirimiphos M |
| 142. | Promecarb |
| 143. | Propaphos |
| 144. | Propoxur |
| 145. | Prothiofos |
| 146. | Prothoat |
| 147. | Pyrachlophos |
| 148. | Pyradaphenthion |
| 149. | Pyresmethrin |
| 150. | Pyrethrum |
| 151. | Pyridaben |
| 152. | Pyrimidifen |
| 153. | Pyriproxyfen |
| 154. | RH 5992 |
| 155. | RH-2485 |
| 156. | Salithion |
| 157. | Sebufos |
| 158. | Silafluofen |
| 159. | Spinosad |
| 160. | Sulfotep |
| 161. | Sulprofos |
| 162. | Tebufenozide |
| 163. | Tebufenpyrad |
| 164. | Tebupirimphos |
| 165. | Teflubenzuron |
| 166. | Tefluthrin |
| 167. | Temephos |
| 168. | Terbam |
| 169. | Terbufos |
| 170. | Tetrachlorvinphos |
| 171. | Thiafenox |
| 172. | Thiodicarb |
| 173. | Thiofanox |
| 174. | Thionazin |
| 175. | Thuringiensin |
| 176. | Tralomethrin |
| 177. | Triarthen |
| 178. | Triazamate |
| 179. | Triazophos |
| 180. | Triazuron |
| 181. | Trichlorfon |
| 182. | Triflumuron |
| 183. | Trimethacarb |
| 184. | Vamidothion |
| 185. | Vetrazine |

| | |
|---|---|
| 186. | XMC (3,5,-Xylylmethylcarbamat) |
| 187. | Xylylcarb |
| 188. | YI 5301/5302 |
| 189. | ζ-Cypermethrin |
| 190. | Zetamethrin |

Non-limitative examples of suitable anthelminthics (dewormer) are named in the following, whereby few of these representatives have insecticidal and acaricidal activity in addition to the anthelminthic activity, and may be already in the listed above.

(A1) Praziquantel=2-cyclohexylcarbonyl-4-oxo-1,2,3,6,7,11b-hexahydro-4H-pyrazino[2,1-α]isoquinoline (A2) Closantel=3,5-diiodo-N-[5-chloro-2-methyl-4-(a-cyano-4-chlorobenzyl)phenyl]-salicylamide (A3) Triclabendazole=5-chloro-6-(2,3-dichlorophenoxy)-2-methylthio-1H-benzimidazole (A4) Levamisol=L-(−)-2,3,5,6-tetrahydro-6-phenylimidazo[2,1b]thiazole (A5) Mebendazole=(5-benzoyl-1H-benzimidazol-2-yl)carbaminic acid methylester (A6) Omphalotin=a macrocyclic fermentation product of the fungus *Omphalotus olearius* described in WO 97/20857

(A7) Abamectin=avermectin B1

(A8) Ivermectin=22,23-dihydroavermectin B1

(A9) Moxidectin=5-O-demethyl-28-deoxy-25-(1,3-dimethyl-1-butenyl)-6,28-epoxy-23-(methoxyimino)-milbemycin B (A10) Doramectin=25-cyclohexyl-5-O-demethyl-25-de(1-methylpropyl)-avermectin A1a (A11) Milbemectin=mixture of milbemycin A3 and milbemycin A4

(A12) Milbemycinoxime=5-oxime of milbemectin

Non-limitative examples of suitable repellents and detachers are:

(R1) DEET (N,N-diethyl-m-toluamide)

(R2) KBR 3023 N-butyl-2-oxycarbonyl-(2-hydroxy)-piperidine (R3) Cymiazole=N,-2,3-dihydro-3-methyl-1,3-thiazol-2-ylidene-2,4-xylidene The said partners in the mixture are best known to specialists in this field. Most are described in various editions of the Pesticide Manual, The British Crop Protection Council, London, and others in the various editions of The Merck Index, Merck & Co., Inc., Rahway, N.J., USA or in patent literature. Therefore, the following listing is restricted to a few places where they may be found by way of example.

(I) 2-Methyl-2-(methylthio)propionaldehyd-O-Methylcarbamoyloxime (Aldicarb), from The Pesticide Manual, 11$^{th}$ Ed. (1997), The British Crop Protection Council, London, page 26;

(II) S-(3,4-Dihydro-4-oxobenzo[d]-[1,2,3]-triazin-3-ylmethyl)O,O-dimethyl-phosphorodithioate (Azinphos-methyl), from The Pesticide Manual, 11$^{th}$ Ed. (1997), The British Crop Protection Council, London, page 67;

(III) Ethyl-N-[2,3-dihydro-2,2-dimethylbenzofuran-7-yloxycarbonyl-(methyl)aminothio]-N-isopropyl-β-alaninate (Benfuracarb), from The Pesticide Manual, 11$^{th}$ Ed. (1997), The British Crop Protection Council, London, page 96;

(IV) 2-Methylbiphenyl-3-ylmethyl-(Z)-(1RS)-cis-3-(2-chlor-3,3,3-trifluorprop-1-enyl)-2,2-dimethylcyclopropancarboxylate (Bifenthrin), from The Pesticide Manual, 11$^{th}$ Ed. (1997), The British Crop Protection Council, London, page 118;

(V) 2-tert-Butylimino-3-isopropyl-5-phenyl-1,3,5-thiadiazian-4-one (Buprofezin), from The Pesticide Manual, 11$^{th}$ Ed. (1997), The British Crop Protection Council, London, page 157;

(VI) 2,3-Dihydro-2,2-dimethylbenzofuran-7-yl-methylcarbamate (Carbofuran), from The Pesticide Manual, 11$^{th}$ Ed. (1997), The British Crop Protection Council, London, page 186;

(VII) 2,3-Dihydro-2,2-dimethylbenzofuran-7-yl-(dibutylaminothio)methylcarbamate (Carbosulfan), from The Pesticide Manual, 11$^{th}$ Ed. (1997), The British Crop Protection Council, London, page 188;

(VIII) S,S'-(2-Dimethylaminotrimethylene)-bis(thiocarbamate) (Cartap), from The Pesticide Manual, 11$^{th}$ Ed. (1997), The British Crop Protection Council, London, page 193;

(IX) 1-[3,5-Dichloro-4-(3-chloro-5-trifluoromethyl-2-pyridyloxy)phenyl]-3-(2,6-difluorobenzoyl)-urea (Chlorfluazuron), from The Pesticide Manual, 11$^{th}$ Ed. (1997), The British Crop Protection Council, London, page 213;

(X) O,O-Diethyl-O-3,5,6-trichloro-2-pyridyl-phosphorothioate (Chlorpyrifos), from The Pesticide Manual, 11$^{th}$ Ed. (1997), The British Crop Protection Council, London, page 235;

(XI) (RS)-α-Cyano-4-fluoro-3-phenoxybenzyl-(1RS,3RS;1RS,3RS)-3-(2,2-dichlorovinyl)-2,2-di-methylcyclopropancarboxylate (Cyfluthrin), from The Pesticide Manual, 11$^{th}$ Ed. (1997), The British Crop Protection Council, London, page 293;

(XII) Mixture of (S)-α-Cyano-3-phenoxybenzyl-(Z)-(1R,3R)-3-(2-chloro-3,3,3-trifluoro-propenyl)-2,2-dimethylcyclopropanecarboxylate and (R)-α-cyano-3-phenoxybenzyl-(Z)-(1R,3R)-3-(2-chloro-3,3,3-trifluoropropenyl)-2,2-dimethylcyclopropanecarboxylate (Lambda-Cyhalothrin), from The Pesticide Manual, 11$^{th}$ Ed. (1997), The British Crop Protection Council, London, page 300;

(XIII) Racemate consisting of (S)-α-cyano-3-phenoxybenzyl-(1R,3R)-3-(2,2-dichlorovinyl)-2,2-dimethylcyclopropanecarboxylate and (R)-α-cyano-3-phenoxybenzyl-(1S,3S)-3-(2,2-dichlorovinyl)-2,2-dimethylcyclopropanecarboxylate (Alpha-cypermethrin), from The Pesticide Manual, 11$^{th}$ Ed. (1997), The British Crop Protection Council, London, page 308;

(XIV) Mixture of the stereoisomers of (S)-α-cyano-3-phenoxybenzyl (1RS,3RS,1RS,3RS)-3-(2,2-dichlorovinyl)-2,2-dimethylcyclopropanecarboxylate (zeta-Cypermethrin), from The Pesticide Manual, 11$^{th}$ Ed. (1997), The British Crop Protection Council, London, page 314;

(XV) (S)-α-cyano-3-phenoxybenzyl-(1R,3R)-3-(2,2-dibromovinyl)-2,2-dimethylcyclopropanecarboxylate (Deltamethrin), from The Pesticide Manual, 11$^{th}$ Ed. (1997), The British Crop Protection Council, London, page 344;

(XVI) (4-Chlorophenyl)-3-(2,6-difluorobenzoyl)urea (Diflubenzuron), from The Pesticide Manual, 11$^{th}$ Ed. (1997), The British Crop Protection Council, London, page 395;

(XVII) (1,4,5,6,7,7-Hexachloro-8,9,10-trinorborn-5-en-2,3-ylenbismethylene)-sulphite (Endosulfan), from The Pesticide Manual, 11$^{th}$ Ed. (1997), The British Crop Protection Council, London, page 459;

(XVIII) α-Ethylthio-o-tolyl-methylcarbamate (Ethiofencarb), from The Pesticide Manual, 11$^{th}$ Ed. (1997), The British Crop Protection Council, London, page 479;

(XIX) O,O-Dimethyl-O-4-nitro-m-tolyl-phosphorothioate (Fenitrothion), from The Pesticide Manual, 11$^{th}$ Ed. (1997), The British Crop Protection Council, London, page 514;

(XX) 2-sec-Butylphenyl-methylcarbamate (Fenobucarb), from The Pesticide Manual, 11$^{th}$ Ed. (1997), The British Crop Protection Council, London, page 516;

(XXI) (RS)-α-Cyano-3-phenoxybenzyl-(RS)-2-(4-chlorophenyl)-3-methylbutyrate (Fenvalerate), from The Pesticide Manual, 11$^{th}$ Ed. (1997), The British Crop Protection Council, London, page 539;

(XXII) S-[Formyl(methyl)carbamoylmethyl]-O, O-dimethyl-phosphorodithioate (Formothion), from The Pesticide Manual, 11$^{th}$ Ed. (1997), The British Crop Protection Council, London, page 625;

(XXIII) 4-Methylthio-3,5-xylyl-methylcarbamate (Methiocarb), from The Pesticide Manual, 11$^{th}$ Ed. (1997), The British Crop Protection Council, London, page 813;

(XXIV) 7-Chlorbicyclo[3.2.0]hepta-2,6-dien-6-yl-dimethylphosphate (Heptenophos), from The Pesticide Manual, 11$^{th}$ Ed. (1997), The British Crop Protection Council, London, page 670;

(XXV) 1-(6-Chloro-3-pyridylmethyl)-N-nitroimidazolidin-2-ylidenamine (Imidacloprid), from The Pesticide Manual, 11$^{th}$ Ed. (1997), The British Crop Protection Council, London, page 706;

(XXVI) 2-Isopropylphenyl-methylcarbamate (Isoprocarb), from The Pesticide Manual, 11$^{th}$ Ed. (1997), The British Crop Protection Council, London, page 729;

(XXVII) O,S-Dimethyl-phosphoramidothioate (Methamidophos), from The Pesticide Manual, 11$^{th}$ Ed. (1997), The British Crop Protection Council, London, page 808;

(XXVIII) S-Methyl-N-(methylcarbamoyloxy)thioacetimidate (Methomyl), from The Pesticide Manual, 11$^{th}$ Ed. (1997), The British Crop Protection Council, London, page 815;

(XXIX) Methyl-3-(dimethoxyphosphinoyloxy)but-2-enoate (Mevinphos), from The Pesticide Manual, 11$^{th}$ Ed. (1997), The British Crop Protection Council, London, page 844;

(XXX) O,O-Diethyl-O-4-nitrophenyl-phosphorothioate (Parathion), from The Pesticide Manual, 11$^{th}$ Ed. (1997), The British Crop Protection Council, London, page 926;

(XXXI) O,O-Dimethyl-O-4-nitrophenyl-phosphorothioate (Parathion-methyl), from The Pesticide Manual, 11$^{th}$ Ed. (1997), The British Crop Protection Council, London, page 928;

(XXXII) S-6-Chloro-2,3-dihydro-2-oxo-1,3-benzoxazol-3-ylmethyl-O,O-diethyl-phosphor-dithioate (Phosalone), from The Pesticide Manual, 11$^{th}$ Ed. (1997), The British Crop Protection Council, London, page 963;

(XXXIII) 2-Dimethylamino-5,6-dimethylpyrimidin-4-yl-dimethylcarbamate (Pirimicarb), from The Pesticide Manual, 11$^{th}$ Ed. (1997), The British Crop Protection Council, London, page 985;

(XXXIV) 2-Isopropoxyphenyl-methylcarbamate (Propoxur), from The Pesticide Manual, 11$^{th}$ Ed. (1997), The British Crop Protection Council, London, page 1036;

(XXXV) 1-(3,5-Dichloro-2,4-difluorophenyl)-3-(2,6-difluorobenzoyl)urea (Teflubenzuron), from The Pesticide Manual, 11$^{th}$ Ed. (1997), The British Crop Protection Council, London, page 1158;

(XXXVI) S-tert-butylthiomethyl-O,O-dimethyl-phosphorodithioate (Terbufos), from The Pesticide Manual, 11$^{th}$ Ed. (1997), The British Crop Protection Council, London, page 1165;

(XXXVII) Ethyl-(3-tert.-butyl-1-dimethylcarbamoyl-1H-1,2,4-triazol-5-yl-thio)-acetate, (Triazamate), from The Pesticide Manual, 11$^{th}$ Ed. (1997), The British Crop Protection Council, London, page 1224;

(XXXVIII) Abamectin, from The Pesticide Manual, 11$^{th}$ Ed. (1997), The British Crop Protection Council, London, page 3;

(XXXIX) 2-sec-butylphenyl-methylcarbamate (Fenobucarb), from The Pesticide Manual, 11$^{th}$ Ed. (1997), The British Crop Protection Council, London, page 516;

(XL) N-tert.-butyl-N'-(4-ethylbenzoyl)-3,5-dimethylbenzohydrazide (Tebufenozide), from The Pesticide Manual, 11$^{th}$ Ed. (1997), The British Crop Protection Council, London, page 1147;

(XLI) (±)-5-Amino-1-(2,6-dichloro-α,α,α-trifluoro-p-tolyl)-4-trifluoromethyl-sulphinylpyrazol-3-carbonitrile (Fipronil), from The Pesticide Manual, 11$^{th}$ Ed. (1997), The British Crop Protection Council, London, page 545;

(XLII) (RS)-α-cyano-4-fluoro-3-phenoxybenzyl(1RS,3RS; 1RS,3RS)-3-(2,2-dichlorovinyl)-2,2-dimethylcyclopropanecarboxylate (beta-Cyfluthrin), from The Pesticide Manual, 11$^{th}$ Ed. (1997), The British Crop Protection Council, London, page 295;

(XLIII) (4-Ethoxyphenyl)-[3-(4-fluoro-3-phenoxyphenyl)propyl](dimethyl)silane (Silafluofen), from The Pesticide Manual, 11$^{th}$ Ed. (1997), The British Crop Protection Council, London, page 1105;

(XLIV) tert.-butyl(E)-α-(1,3-dimethyl-5-phenoxypyrazol-4-yl-methylenamino-oxy)-p-toluate (Fenpyroximate), from The Pesticide Manual, 11$^{th}$ Ed. (1997), The British Crop Protection Council, London, page 530;

(XLV) 2-tert.-butyl-5-(4-tert.-butylbenzylthio)-4-chloropyridazin-3(2H)-one (Pyridaben), from The Pesticide Manual, 11$^{th}$ Ed. (1997), The British Crop Protection Council, London, page 1161;

(XLVI) 4-[[4-(1,1-dimethylphenyl)phenyl]ethoxy]-quinazoline (Fenazaquin), from The Pesticide Manual, 11$^{th}$ Ed. (1997), The British Crop Protection Council, London, page 507;

(XLVII) 4-Phenoxyphenyl-(RS)-2-(pyridyloxy)propyl-ether (Pyriproxyfen), from The Pesticide Manual, 11$^{th}$ Ed. (1997), The British Crop Protection Council, London, page 1073;

(XLVIII) 5-Chloro-N-{2-[4-(2-ethoxyethyl)-2,3-dimethylphenoxy]ethyl}-6-ethylpyrimidin-4-amine (Pyrimidifen), from The Pesticide Manual, 11$^{th}$ Ed. (1997), The British Crop Protection Council, London, page 1070;

(XLIX) (E)-N-(6-chloro-3-pyridylmethyl)-N-ethyl-N'-methyl-2-nitrovinylidenediamine (Nitenpyram), from The Pesticide Manual, 11$^{th}$ Ed. (1997), The British Crop Protection Council, London, page 880;

(L) (E)-N$^1$-[(6-chloro-3-pyridyl)methyl]-N$^2$-cyano-N$^1$-methylacetamidine (Nl-25, Acetamiprid), from The Pesticide Manual, 11$^{th}$ Ed. (1997), The British Crop Protection Council, London, page 9;

(LI) Avermectin B$_1$, from The Pesticide Manual, 11$^{th}$ Ed. (1997), The British Crop Protection Council, London, page 3;

(LII) an insect-active extract from a plant, especially (2R,6aS, 12aS)-1,2,6,6a,12,12a-hexhydro-2-isopropenyl-8,9-dimethoxy-chromeno[3,4-b]furo[2,3-h]chromen-6-one (Rotenone), from The Pesticide Manual, 11$^{th}$ Ed. (1997), The British Crop Protection Council, London, page 1097; and an extract from *Azadirachta indica*, especially azadirachtin, from The Pesticide Manual, 11$^{th}$ Ed. (1997), The British Crop Protection Council, London, page 59; and (LIII) a preparation which contains insect-active nematodes, preferably *Heterorhabditis bacteriophora* and *Heterorhabditis megidis*, from The Pesticide Manual, 11$^{th}$ Ed. (1997), The British Crop Protection Council, London, page 671; *Steinernema feltiae*, from The Pesticide Manual, 11$^{th}$ Ed. (1997), The British Crop Protection Council, London, page 1115 and *Steinernema scapterisci*, from The Pesticide Manual, 11$^{th}$ Ed. (1997), The British Crop Protection Council, London, page 1116;

(LIV) a preparation obtainable from *Bacillus subtilis*, from The Pesticide Manual, 11$^{th}$ Ed. (1997), The British Crop Protection Council, London, page 72; or from a strain of *Bacillus thuringiensis* with the exception of compounds isolated from GC91 or from NCTC11821; The Pesticide Manual, 11$^{th}$ Ed. (1997), The British Crop Protection Council, London, page 73;

(LV) a preparation which contains insect-active fungi, preferably *Verticillium lecanii*, from The Pesticide Manual, 11$^{th}$ Ed. (1997), The British Crop Protection Council, London, page 1266; *Beauveria brogniartii*, from The Pesticide Manual, 11$^{th}$ Ed. (1997), The British Crop Protection Council, London, page 85 and *Beauveria bassiana*, from The Pesticide Manual, 11$^{th}$ Ed. (1997), The British Crop Protection Council, London, page 83;

(LVI) a preparation which contains insect-active viruses, preferably Neodipridon Sertifer NPV, from The Pesticide Manual, 11$^{th}$ Ed. (1997), The British Crop Protection Council, London, page 1342; *Mamestra brassicae* NPV, from The Pesticide Manual, 11$^{th}$ Ed. (1997), The British Crop Protection Council, London, page 759 and *Cydia pomonella granulosis* virus, from The Pesticide Manual, 11$^{th}$ Ed. (1997), The British Crop Protection Council, London, page 291;

(CLXXXI) 7-Chloro-2,3,4a,5-tetrahydro-2-[methoxycarbonyl(4-trifluoromethoxyphenyl)-carbamoyl]indole[1,2e] oxazolin-4a-carboxylate (DPX-MP062, Indoxycarb), from The Pesticide Manual, 11$^{th}$ Ed. (1997), The British Crop Protection Council, London, page 453;

(CLXXXII) N'-tert.-butyl-N'-(3,5-dimethylbenzoyl)-3-methoxy-2-methylbenzohydrazide (RH-2485, Methoxyfenozide), from The Pesticide Manual, 11$^{th}$ Ed. (1997), The British Crop Protection Council, London, page 1094; and (CLXXXIII) (N'-[4-methoxy-biphenyl-3-yl]-hydrazinecarboxylic acid isopropyl ester (D 2341), from Brighton Crop Protection Conference, 1996, 487-493;

(CLXXXIV) Spinosad is a mixture of Spinosyn A and Spinosyn D; U.S. Pat. No. 5,362,634;

(R2) Book of Abstracts, 212th ACS National Meeting Orlando, Fla., Aug. 25-29 (1996), AGRO-020. Publisher: American Chemical Society, Washington, D.C. CONEN: 63BFAF.

As a consequence of the above details, a further essential aspect of the present invention relates to combination preparations for the simultaneous treatment of inflammatory conditions and the control of economically important parasites on warm-blooded non-human animals, characterized in that veterinary compositions contain, in addition to a compound of formula I, at least one further active ingredient having the same or different sphere of activity and at least one physiologically acceptable carrier. The present invention is not restricted to two-fold combinations.

It is another important objective of the present invention to provide a pharmaceutical composition comprising a therapeutically effective amount of a compound of the formula I or a physiologically acceptable ester or salt thereof together with a physiologically acceptable carrier. This pharmaceutical composition is very suitable for treating acute and chronic inflammation in humans and animals and shows a very positive curing effect with regard to the bone-related diseases discussed above.

In a preferred embodiment said pharmaceutical composition is administered via a systemic route, for example parenterally or preferably orally to humans or animals either as a prophylactic or preferably curative treatment.

It is a further target of this invention to provide a therapeutic composition for the protection, treatment and repair of connective tissue in non-human animals and a method for the treatment of connective tissue in a human or animal patient.

An important part of the present invention is a pharmaceutical composition for oral administration which, when ingested, is effective in treating pain and discomfort of inflammatory ailments such as, but not limited to, rheumatoid arthritis, osteoarthritis, hip dysplasia, juvenile rheumatoid arthritis, soft tissue rheumatism, gout, low back pain, afflictions, sprains, headache, backache, and general muscle soreness after exercise and exertion.

It is still another object of the present invention to provide a composition to be administered orally which improves the general health, quality of life, and well being of those humans and animals suffering from chronic inflammatory diseases, including rheumatism and arthritis.

It is a yet further object of the present invention to provide a safe and effective composition which can be used to reduce the dosage of, or replace synthetic Non-Steroidal Anti-Inflammatory Drugs (NSAIDs), for the symptomatic treatment of pain, inflammation and swelling in humans and animals.

It is also an object of the present invention to provide a safe and effective composition for the treatment of pain, inflammation and swelling in individuals for whom NSAIDs are no longer desirable due to gastro-toxicity, gut intolerance and risk of renal damage.

It is a further object of the present invention to provide a composition which is formulated using rigorously and correctly identified, analyzed, and documented biological respectively botanical ingredients from which active ingredients have been extracted to prepare a concentrate, which results in the end composition standardized to contain minimum levels of certain indicator chemicals having the desired physiological attributes.

Preferred embodiments of the present invention are:

A pharmaceutical composition comprising an effective amount of a compound of the formula I together with a physiologically acceptable carrier.

A pharmaceutical composition comprising in addition to an effective amount of standardized extract of White Willow Bark, Green-lipped Mussel, Boswellic Acid, glucosamine, and/or chondroitin sulfate.

More preferred is a dosage form comprising a daily dosage of the compound of the formula I from about 0.1 to about 500 mg/kg/day, preferably 1 to about 500 mg/kg/day, more preferably from about 0.1 to about 100 mg/kg/day, more preferably 2 to about 100 mg/kg/day, even more preferably from about 2 to about 25 mg/kg/day.

Advantageously said pharmaceutical composition is a veterinary composition.

A preferred embodiment of this invention consists in a pharmaceutical composition comprising a daily dosage of about 10 to about 500 mg/kg Willow Bark, of about 10 to about 500 mg/kg Mussel Extract and of about 2 to about 100 mg/kg Boswellic acids.

Even more preferred is such a pharmaceutical composition if it comprises in addition a daily dosage of 1 to 400 mg/kg glucosamine and/or 1 to 500 mg/kg chondroitin sulfate.

A preferred embodiment consists of a method for the prevention, metaphylaxis or treatment of osteoarthritis in a non-human animal and/or for reducing inflammation and pain associated with acute inflammation of body parts. This method comprises the administration of a composition as set out before.

Another preferred embodiment consists of the use of one of said veterinary compositions in a method for the prevention, metaphylaxis or treatment of osteoarthritis in a human or an animal.

Preferred is also the use of a compound of the formula I in the manufacture of a pharmaceutical composition, preferably for the prevention, metaphylaxis or treatment of osteoarthritis in a human or an animal, especially for reducing inflammation and pain associated with acute inflammation of body parts and/or for reducing inflammation and pain associated with acute inflammation of body parts, particularly joints, due to injury or due to arthritic conditions or other disease conditions.

A further preferred embodiment is a such a pharmaceutical composition for the prevention, metaphylaxis or treatment of osteoarthritis.

Preferred are furthermore methods for the prevention, metaphylaxis and treatment of osteoarthritis in a human or an animal comprising a composition as defined above to said human or animal.

The preferred treatment is the oral administration of one of the described compounds of the formula I either alone or in combination with another beneficial component and preferably in the form of a pharmaceutical compositions.

It goes without saying that the active ingredients of the present invention can be combined with further beneficial substances, such as vitamins, e.g. from the B series or manganese salts.

In another preferred embodiment of the present invention the dosage form for oral treatment may consist of one or more capsules or tablets for animal oral consumption. The dosage ranges defined herein before are meant per 1 Kg bodyweight per day. This dosage may be administered in a single daily dosage form in which all components are present. Alternatively, the nutritional supplement compositions for the present invention may be administered more than once, preferably twice, per day. The number of daily administrations will depend upon the needs of the non-human animal recipient. Different connective tissue disorders and injuries may require different amounts of the compositions of the present invention. In those regards, several dosages may be administered depending on the particular needs of the non-human animal.

These pharmaceutical compositions of the present invention may be made by conventional methods. For example, the above-described ingredients are combined as the active ingredient in intimate admixture with at least one suitable carrier according to conventional formulation techniques. The carrier must be a physiologically acceptable carrier and may take a wide variety of forms depending upon the form of preparation desired for administration.

In preparing the veterinary compositions in oral dosage form, any usual veterinary medium may be employed. For oral liquid preparations (e.g., suspensions, elixirs, feed additive, and solutions), media containing for example, water, oils, alcohols, flavoring agents, preservatives, coloring agents and the like may be used. Physiologically acceptable carriers such as starches, sugars, diluents, granulating agents, lubricants, binders, disintegrating agents, and the like may be used to prepare solid oils (e.g. powders, capsules, pills, caplets, tablets, microencapsulated granules, micro-tablets, coated granules and lozenges). Capsules or tablets are the preferred oral dosage form. Controlled release forms may also be used. Because of their ease in administration, lozenges, tablets, pills, caplets, and capsules represent the most advantageous oral dosage unit form, in which case solid veterinary carriers are obviously employed. If desired, tablets may be sugar coated or enteric coated by standard techniques. A preferred dosage form consists of highly palatable tablets consisting of a palatable matrix wherein the active ingredient is incorporated in a taste-masked form. The compositions of the present invention may be in form of one or more of these oral dosage forms, i.e. a single dosage may be in multiple forms.

For the formulation of compositions that are to be administered to humans or animals, such as domestic animals, livestock, and pets, the adjuvants and carriers known from the medical and veterinary practice for oral galenic forms can be used.

Suitable physiologically acceptable carriers are in particular fillers, such as sugars, e.g. lactose, saccharose, mannitol or sorbitol, cellulose preparations and/or calcium phosphates, e.g. tricalcium phosphate or calcium hydrogen phosphate, in a broader sense also binders, such as starch pastes using e.g. corn, wheat, rice or potato starch, gelatin, tragacanth, methyl cellulose and/or, if desired, disintegrants, such as the abovementioned starches, in a broader sense also carboxymethyl starch, cross-linked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Tablet cores may be provided with suitable, where appropriate enteric, coatings, using inter alia concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes, flavours or pigments may be added to the tablets or tablet coatings, for example for identification purposes or to indicate different doses of active ingredient.

Further orally administrable compositions include hard capsules consisting of gelatine, and also soft, sealed capsules consisting of gelatine and a plasticizer, such as glycerol or sorbitol. The hard capsules may contain the active ingredient in the form of granules, for example in admixture with fillers, such as lactose, binders, such as starches, and/or glidants, such as talc or magnesium stearate, and where appropriate stabilizers. In soft capsules, the active ingredients are preferably dissolved or suspended in suitable liquids, such as fatty oils, paraffin oil, or liquid polyethylene glycols, and stabilizers may likewise be added. Amongst other forms, capsules, which can be both easily chewed and also swallowed whole, are preferred.

The compositions of the invention can be prepared in a known manner, e.g. for example by means of conventional mixing, granulating, coating, dissolving or lyophilizing methods. Pharmaceutical compositions for oral administration can be obtained, for example, by combining the active ingredients with solid carriers, granulating a resulting mixture where appropriate, and processing the mixture or granules, if desired or necessary, to form tablets or tablet cores following the addition of suitable excipients.

Natural additional active ingredients like Willow Bark, Mussel Extract and Boswellic acid are used in these compositions in standardized solid form and preferably together with—at least—one of the adjuvants conventionally employed in the art of formulation, such as extenders, e.g. solvents or solid carriers, or surface-active compounds (surfactants). For usage in humans and animals, such as domestic animals, livestock, and pets of course only physiologically acceptable adjuvants are used.

It goes without saying that the compounds of the formula I of the present invention can be combined with further beneficial substances, such as vitamins, e.g. from the B series or manganese salts.

Alternatively, and of particular use in large animals, the pharmaceutical compositions for the present invention may for example be administered in scoops. These preparations may be made by conventional methods. For example, to prepare the pharmaceutical compositions of the invention, one or more compounds of the formula I in intimate admixture with a suitable carrier according to conventional compounding techniques. The carrier may take a wide variety of forms depending upon the form of preparation desired for administration, e.g., oral, sublingual, nasal, guttural, rectal, transdermal or parenteral.

In preparing the compositions in oral dosage form, any usual pharmaceutical medium may be employed. For oral liquid preparations (e.g. suspensions, elixirs, feed additive, and solutions), media containing for example, water, oils, alcohols, flavoring agents, preservatives, coloring agents and the like may be used. Carriers such as starches, sugars, diluents, granulating agents, lubricants, binders, disintegrating agents, and the like may be used to prepare solid oils (e.g., powders, capsules, pills, caplets, tablets, microencapsulated granules, micro-tablets, coated granules and lozenges). Capsules or tablets are the preferred oral dosage form. Controlled release forms may also be used. Because of their ease in administration, lozenges, tablets, pills, caplets, and capsules represent the most advantageous oral dosage unit form, in which case solid pharmaceutical carriers are obviously employed. If desired, tablets may be sugar coated of enteric coated by standard techniques. The compositions of the present invention may be in form of one or more of these oral dosage forms, i.e. a single dosage may be in multiple forms.

For parenteral products, the carrier will usually comprise sterile water, although other ingredients may be included, e.g. to aid solubility or for the preservation purposes. Injectable suspensions may also be prepared, in which case appropriate liquid carriers, suspending agents, and the like may be employed.

For the formulation of compositions that are to be administered to humans, domestic animals, livestock, and pets, the adjuvants known from the medical and veterinary practice for oral, parenteral and implant forms can be used.

Suitable carriers are in particular fillers, such as sugars, e.g. lactose, saccharose, mannitol or sorbitol, cellulose preparations and/or calcium phosphates, e.g. tricalcium phosphate or calcium hydrogen phosphate, in a broader sense also binders, such as starch pastes using e.g. corn, wheat, rice or potato starch, gelatin, tragacanth, methyl cellulose and/or, if desired, disintegrants, such as the above-mentioned starches, in a broader sense also carboxymethyl starch, cross-linked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Tablet cores may be provided with suitable, where appropriate enteric, coatings, using inter alia concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes, flavours or pigments may be added to the tablets or tablet coatings, for example for identification purposes or to indicate different doses of active ingredient.

Further orally administrable pharmaceutical compositions include hard capsules consisting of gelatine, and also soft, sealed capsules consisting of gelatine and a plasticizer, such as glycerol or sorbitol. The hard capsules may contain the active ingredient in the form of granules, for example in admixture with fillers, such as lactose, binders, such as starches, and/or glidants, such as talc or magnesium stearate, and where appropriate stabilizers. In soft capsules, the active ingredients are preferably dissolved or suspended in suitable liquids, such as fatty oils, paraffin oil, or liquid polyethylene glycols, and stabilizers may likewise be added. Amongst other forms, capsules, which can be both easily chewed and also swallowed whole, are preferred.

The formulations suitable for parenteral administration are especially aqueous solutions of the active ingredients in water-soluble form, e.g. water-soluble salts, in the broader sense also suspensions of the active ingredients, such as appropriate oily injectable suspensions using suitable lipophilic solvents or vehicles, such as oils, e.g. sesame oil, or synthetic fatty acid esters, e.g. ethyl oleate, or triglycerides, or aqueous injectable suspensions containing viscosity-increasing agents, e.g. sodium carboxymethyl cellulose, sorbitol and/or dextran, and where appropriate stabilizers.

The pharmaceutical compositions (drugs) of the invention can be prepared in a known manner, e.g. for example by means of conventional mixing, granulating, coating, dissolving or lyophilizing methods. Pharmaceutical compositions for oral administration can be obtained, for example, by combining the active ingredients with solid carriers, granulating a resulting mixture where appropriate, and processing the mixture or granules, if desired or necessary, to form tablets or tablet cores following the addition of suitable excipients. The active ingredients are used in these compositions in pure form and a solid active ingredient e.g. in a specific particle size, or preferably together with—at least—one of the adjuvants conventionally employed in the art of formulation, such as extenders, e.g. solvents or solid carriers, or surface-active compounds (surfactants). For usage in humans, domestic animals, livestock, and pets of course only physiologically acceptable adjuvants are used.

Pharmaceutical compositions (drugs) for humans or animals also form the most important aspect of the invention.

Having discussed of the present invention, it will be more clearly perceived and better understood from the following specific formulation examples, which are intended to provide illustrative but not limiting examples. They represent preferred embodiments of the present.

The advantages of the invention will become more fully apparent from the description and claims, which follow, or may be learned by practicing the invention.

In the following formulation examples of use in men, domestic animals, livestock, and pets, the term "active ingredient" is understood to mean one or more of the active ingredients named in claim 1, preferably the compound [2,7-Dichloro-10-methoxy-3-thia-9-aza-benzo[f]azulen-(4Z)-ylidene]-acetic acid

FORMULATION EXAMPLES

Example F1

Tablets: Containing a Compound of the Formula I can be Prepared as Follows

| Composition (for 1000 tablets) | |
| --- | --- |
| Active ingredient | 25 g |
| Lactose | 100.7 g |
| Wheat starch | 6.25 g |
| Polyethylene glycol 6000 | 5.0 g |
| Talc | 5.0 g |
| Magnesium stearate | 1.8 g |
| Deionized water | q.s. |

Preparation: All solid ingredients are first passed through a sieve with a mesh size of 0.6 mm. The active ingredient, the lactose, the talc, and half the starch are then mixed. The other half of the starch is suspended in 40 ml water, and this suspension is added to a boiling solution of the polyethylene glycol in 100 ml water. The resulting starch paste is added to the mixture, and this is then granulated, water being added where appropriate. The granulate is dried overnight at 35°, passed through a sieve with a mesh size of 1.2 mm, mixed with the magnesium stearate, and compressed to form tablets concave on both sides and with a diameter of 6 mm.

Tablets: (each containing a total of 0.0183 g active ingredient) are prepared as follows:

| Composition (for 10,000 tablets) | |
| --- | --- |
| Active ingredient | 183.00 g |
| Lactose | 290.80 g |
| Potato starch | 274.70 g |
| Stearic acid | 10.00 g |
| Talc | 217.00 g |
| Magnesium stearate | 2.50 g |
| Colloidal silica | 32.00 g |
| Ethanol | q.s. |

A mixture of the active ingredient, the lactose and 274.70 g potato starch is wetted with an ethanolic solution of stearic acid and granulated through a sieve. After drying, the remaining potato starch, the talc, the magnesium stearate, and the colloidal silica are added and the mixture compressed to form tablets of 0.1 g each in weight, which—if so desired—can be scored to allow for a finer adjustment of the dose.

Example F2

Capsules: Each Containing a Total of 0.022 g Active Ingredient can be Prepared as Follows

| Composition (for 1000 capsules) | |
| --- | --- |
| Active ingredient | 22.00 g |
| Lactose | 249.80 g |
| Gelatin | 2.00 g |
| Corn starch | 10.00 g |
| Talc | 15.00 g |
| Water | q.s. |

The active ingredient is mixed with the lactose, the mixture wetted evenly with an aqueous solution of the gelatine and granulated through a sieve with a mesh size of 1.2-1.5 mm. The granulate is mixed with the dried cornstarch and the talc, and portions of 300 mg are filled into hard gelatine capsules (size 1).

Example F3

Premix (Feed Additive)

| | |
| --- | --- |
| 0.16 | parts by weight of active ingredient |
| 4.84 | parts by weight of secondary calcium phosphate, alumina, aerosil, carbonate or calcium carbonate are mixed until homogeneous with |
| 95 | parts by weight of an animal feed |
| or | |
| 0.41 | parts by weight of active ingredient |
| 5.00 | parts by weight of aerosil/calcium carbonate (1:1) are mixed until homogeneous with |
| 94.59 | parts by weight of a commercially available feed. |

Example F4

Boli

| | | |
| --- | --- | --- |
| I | Active ingredient | 33.00% |
| | Methylcellulose | 0.80% |
| | Silicic acid, highly dispersed | 0-80% |
| | Corn starch | 8.40% |
| or | | |
| II | Active ingredient | 16.00% |
| | Lactose, crystalline | 22.50% |
| | Corn starch | 17.00% |
| | Microcrystalline cellulose | 16.50% |
| | Magnesium stearate | 1.00% |

The methylcellulose is first stirred into water. After the material has swollen, the silicic acid is stirred in and the mixture homogeneously suspended. The active ingredient and the cornstarch are mixed. The aqueous suspension is worked into this mixture and kneaded to dough. The resulting mass is granulated through a 12 M sieve and dried. In a further step, all 4 adjuvants are thoroughly mixed. Finally, the premixtures resulting from the first two partial steps are mixed and compressed to form boli.

Example F5

Injectables

| A. Oily vehicle (slow release) | |
| --- | --- |
| Active ingredient | 0.1-1.0 g |
| Groundnut oil | ad 100 ml |
| or | |
| Active ingredient | 0.1-1.0 g |
| Sesame oil | ad 100 ml |

Preparation: The active ingredient is dissolved in part of the oil with stirring and where appropriate gentle heating, then made up to the desired volume and sterile-filtered through a suitable membrane filter with a pore size of 0.22 μm.

The following examples of preparation and application serve to explain the invention without limiting it to the individual aspects of these examples.

Example F6

Solutions (for Dilution with Drinking Water)

15% active ingredient in 2,2-dimethyl-4-hydroxy methyl1-1,3-dioxolane
10% active ingredient in diethylene glycol monethyl ether
10% active ingredient in polyethylene glycol (mol. wt. 300)
5% active ingredient in glycerol

Example F7

Soluble Powder 25 parts of active ingredient
1 part of sodium lauryl sulfate
3 parts of colloidal silica
71 parts of urea The constituents are mixed and the mixture is finely ground in a suitable mill. Other biocidal active ingredients or agents, which are inert towards the active ingredients and acceptable to men or animals to be treated, or mineral salts or vitamins, can be admixed to the compositions described.

Many modifications may be made without departing the basic spirit of the present invention. Accordingly, it will be appreciated to those skilled in the art that within the scope of the attended claims, the invention may be practiced other than has been specifically described herein.

Veterinary compositions (drugs) for non-human animals form a very important aspect of the invention.

The following preparation examples are illustrative of the preparation process of the present invention but do not limit it to the specific compounds and processes conditions.

PREPARATION EXAMPLES

Example P1

Preparation of
7-Chloro-2-ethoxy-benzo[d][1,3]oxazin-4-one

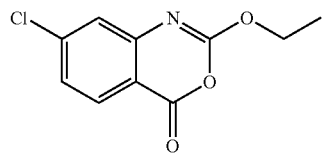

A 4-necked, round-bottomed flask, equipped with a mechanical stirrer, digital thermometer, addition funnel and a condenser with nitrogen inlet-outlet is charged with ethyl-chloroformate (2.21 kg) and acetonitrile (1.97 kg). The clear solution is cooled down to −10° C. and a solution of 4-chloroanthranylic acid (1 kg) in pyridine (2.42 kg) is added over 2 hours at −10° C. Afterwards stirring is maintained for 1 hour. The temperature is slowly raised to 10° C., and toluene (3.47 kg) is added over 10 min at 15° C., followed by deionized water (4 kg), added over 5 min at 15° C. The mixture is stirred at 15° C. for 5 min and left to settle over 10 min. The bottom aqueous layer is discarded and deionized water (2 kg) is added over 5 min with efficient stirring at 15° C. After 5 min stirring, the mixture is left to settle over 10 min and the bottom aqueous layer is discarded. The washing is repeated twice with 2 kg of water. The toluene is distilled off at 35° C. under reduced pressure (20-40 mbar). To the resulting mixture (2 L) heptane (3 L) is added over 5 min. The mixture is stirred and cooled to an internal temperature of −10° C. over a period of 40 min. The mixture is stirred at this temperature for an additional 1 h. Then the solid is collected by filtration, washed with heptane (2×1 L) and dried under vacuum (80-100 mbar) at 45° C. The crude product obtained by this way, having a melting point of 83-88° C., is used as it for the next step.

Example P2

Preparation of 7-Chloro-9H-3-thia-9-aza-benzo[f]
azulene-4,10-dione

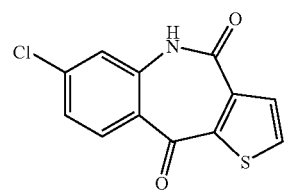

A 4-necked, round-bottomed flask, equipped with a mechanical stirrer, digital thermometer, addition funnel and a condenser with nitrogen inlet-outlet is charged with thiophen-3-carboxylic acid (448.2 g) and tetrahydrofuran (4.7 L) and stirred to dissolution. The solution is cooled to 0° C. and diisopropylamine (245 mL) is added over 5 min. Then, a 1.6M solution of butyl lithium in hexane (4.8 L) is added over 2.5 hours while maintaining the internal temperature at 0° C. The mixture is stirred for an additional hour before being cooled to −65° C. Then 7-Chloro-2-ethoxy-benzo[d][1,3]oxazin-4-one (830 g), dissolved in tetrahydrofuran (1.7 L) is added over 1 hour. The mixture is stirred at −65° C. for 1 hour, then warmed to 0° C. over 40 min and stirred for 30 min. Then water (4 L) is added over 10 min letting the temperature be raised to 20° C. The mixture is stirred at this temperature for 16 hours before being concentrated under reduced pressure to remove the organic solvents. To the residue ethanol (11 L) and lithium hydroxide (295.5 g) are added. The mixture is heated to 60° C. over 45 min, stirred at this temperature for 3 hours, then the temperature is raised to 75° C. over 10 min and hydrochloric acid (2 L, 37% m/m) is added over 10 min under gentle reflux. The mixture is stirred for an hour at 60-65° C. The suspension is then cooled to room temperature and the solid is collected, washed 5 times with water (4.2 L total), ethanol (5 L total) and dried under vacuum (60° C., 50 mbar) to yield the title compound with a melting point of >280° C.

Example P3

Preparation of 7-Chloro-10-methoxy-3-thia-9-aza-
benzo[f]azulen-4-one

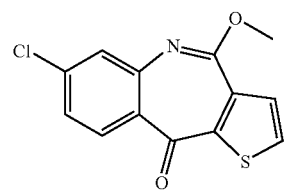

A 4-necked, round-bottomed flask, equipped with a mechanical stirrer, digital thermometer, addition funnel and a condenser with nitrogen inlet-outlet is charged with 7-Chloro-9H-3-thia-9-aza-benzo[f]azulene-4,10-dione (559.6 g), toluene (6.8 kg) and dimethylformamide (100.73 g). To the stirred suspension phosphorus oxychloride (357.2 g) is added over 5 min at 20-25° C. The pipes are flushed with toluene (774 g), then the temperature is raised to 108° C. over 1 hour and stirring continued for about 5 hours. Then the mixture is cooled to −5° C. and a 30% solution of sodium methylate (1.43 kg) is added over 30 min at −5° C. After addition the mixture is warmed to 40° C. over an hour and the solvent is distilled at 20-45° C. under reduced pressure. To the residue deionized water (6.7 kg) is added and the mixture is concentrated under reduced pressure to 7 L. Then heptane (3.06 kg) is added and the temperature is raised to 70° C. over 1 hour, followed by additional stirring of 10 min. The suspension is then cooled to 0° C. and the solid is collected by filtration, washed with heptane (2×383 g) and deionized water (2×1.1 kg) and dried under vacuum at 65° C. to yield the title compound with a melting point of >195-197° C.

Example P4

Preparation of [7-Chloro-10-methoxy-3-thia-9-aza-benzo[f]azulen-(4Z)-ylidene]-acetic acid

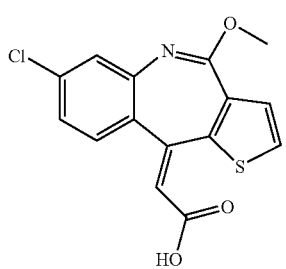

A 4-necked, round-bottomed flask, equipped with a mechanical stirrer, digital thermometer, addition funnel, and a condenser with nitrogen inlet-outlet is charged with lithium hydride (25 g), and dimethyl sulfoxide (3.55 kg). To the suspension trimethylphosphono acetate (574.1 g) is added over 30 min at 20° C. The reaction mixture is stirred at 30° C. for 1 hour, then 7-Chloro-10-methoxy-3-thia-9-aza-benzo[f]azulen-4-one (700 g) is added in one portion using a powder funnel being flushed afterward with dimethyl sulfoxide (306 g). The temperature is raised to 60° C. over 40 min and the mixture is stirred for 5 hours. The reaction is cooled to 25° C. over a period of 30 min and a solution of sodium hydroxide (171.2 g) in deionized water (1.07 kg) is added over 30 min. The mixture is stirred for 30 min then isopropyl acetate (4.3 L) and deionized water (7 kg) are added. The biphasic mixture is stirred at 20-25° C. for 5 min and the bottom aqueous layer separated. To this layer isopropyl acetate (2.7 kg) is added and after 5 min stirring the bottom aqueous layer is separated. To this aqueous layer isopropyl acetate (4.9 kg) is added followed by phosphoric acid (714.5 kg) over 20 min at 20-30° C. (with a final pH of 3-3.5). The mixture is then warmed to 60-65° C. over 60 min and the phases are separated. The organic phase is washed three times with deionized water (2.09 kg), slowly cooled to −10° C. over 2 hours and then stirred for 1 hour allowing partial crystallisation of the undesired isomer. The suspension is filtered and the mother liquor concentrated to a minimum. The latter is diluted with ethanol abs. (3.32 L) and again concentrated to totally remove the isopropyl acetate. The residue is diluted again with ethanol abs. (3.32 L) and dicyclohexylamine (380 g) is added at about 60° C. over a period of 20 min. The clear solution is then cooled to 15° C. over 2 hours and kept at this temperature for 1 hour and finally filtered. The solid is washed with ethanol (2×275 g) and dried at 60° C. under reduced pressure to get the enriched compound [7-Chloro-10-methoxy-3-thia-9-aza-benzo[f]azulen-(4Z)-ylidene]-acetic acid dicyclohexylamine salt.

The latter is suspended in methanol/water 1:1 (9.6) and phosphoric acid 85% (105.1 g) is added. The suspension is heated at 60° C. for 5-10 min, then cooled to 25° C. and stirred for 1 hour. The suspension is filtered and the solid is washed with methanol/water 1:1 (826 mL) and dried under vacuum to afford [7-Chloro-10-methoxy-3-thia-9-aza-benzo[f]azulen-(4Z)-ylidene]-acetic acid with a melting point of 186-188° C.

Example P5

Preparation of [2,7-Dichloro-10-methoxy-3-thia-9-aza-benzo[f]azulen-(4Z)-ylidene]-acetic acid

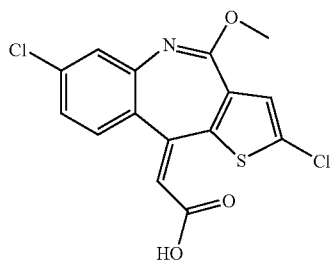

A round-bottomed flask, equipped with a magnetic stirrer, digital thermometer, addition funnel and a condenser with nitrogen inlet-outlet, is charged with diisopropylamine (462.9 mL) and tetrahydrofuran (4.2 L). The solution is cooled to −78° C. and n-butyl lithium (1.71 L, 1.6 M in hexane) is added over a period of 1 hour. After addition the reaction mixture is stirred for 1 hour and [7-Chloro-10-methoxy-3-thia-9-aza-benzo[f]azulen-(4Z)-ylidene]-acetic acid (350 g), dissolved in tetrahydrofuran (1.4 L), is added dropwise over 1 hour while maintaining the temperature at −70° C. Stirring is maintained for 1 hour at −78° C. Afterwards the yellow solution is transferred through a cold tube to a solution of hexachloroethane (779 g), dissolved in tetrahydrofuran (4.2 L), over a period of 45 min while maintaining the temperature at −25° C. The yellow solution is then allowed to slowly warm up to 0° C. over 30 min and kept at this temperature for 30 min. Then, deionized water (2.26 kg) is added over 5 min and the resulting emulsion concentrated under vacuum to remove the solvent. Then tert-butylmethylether (5.25 L) and water (3 L) are added. After vigorous stirring the organic phase is removed and replaced with isopropyl acetate (7 L). Then the mixture is acidified with phosphoric acid (339 L) to get a pH value of 2-3. Afterwards, the organic phase is separated and concentrated to 1/10, methanol (6.2 L) is added and the temperature raised to 65° C. over 40 min. The solution is distilled to a volume of 3.4 L, the resulting suspension cooled to −15° C. and stirred for 1 hour. The crystalline precipitation is collected by filtration, washed with cold methanol (500 mL) and dried under vacuum (50° C., 20-50 mmbar) to yield [2,7-Dichloro-10-methoxy-3-thia-9-aza-benzo[f]azulen-(4Z)-ylidene]-acetic acid with a melting point of 195-197° C.

In the following Me stands for methyl and Et for ethyl.

TABLE 1

Compounds of the formula Ia

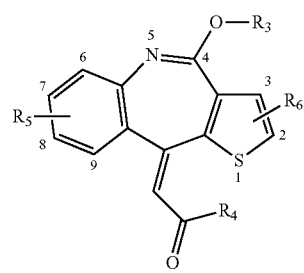

(Ia)

| No | R$_4$ | R$_5$ | R$_6$ | R$_3$ | Olefin configuration |
|---|---|---|---|---|---|
| 1.001 | OH | 7-Cl | H | Me | Z |
| 1.002 | OH | H | H | Me | Z |
| 1.003 | OH | H | H | Me | E |
| 1.004 | OMe | H | H | Me | Z |
| 1.005 | OEt | H | H | Me | Z |
| 1.005 | OEt | H | H | Me | E |
| 1.007 | OH | 7-Cl | 2-Cl | Me | Z |
| 1.008 | OH | 7-Cl | 2-Cl | Me | E |
| 1.009 | OH | H | 2-Cl | Me | E |
| 1.010 | HN—(CH$_2$)$_4$—NH$_2$ | 7-Cl | 2-Cl | Me | Z |
| 1.011 | OH | 7-F | 2-F | Me | Z |
| 1.012 | NH$_2$ | 7-Cl | 2-Cl | Me | Z |
| 1.013 | NHMe | 7-Cl | H | Me | Z |
| 1.014 | SMe | 7-Cl | 2-Cl | Me | Z |
| 1.015 | S(i-propyl) | H | H | Me | Z |
| 1.016 | OH | 7-Cl | 2-Cl | Et | Z |
| 1.017 | OH | 7-Cl | 3-Cl | Me | Z |
| 1.018 | OH | 8-Cl | 2-Cl | Me | Z |
| 1.018 | OEt | 7-Cl | H | Me | E |
| 1.020 | O(n-propyl) | 7-F | H | Et | Z |

MP of 1.007 = 189-192° C. [cis (Z) isomer]
MP of 1.008 = 213-216° C. [trans (E) isomer]

TABLE 2

Compounds of the formula Ib

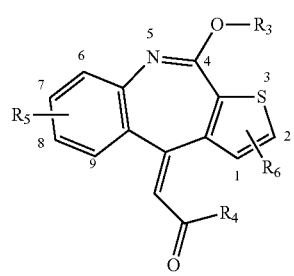

(Ib)

| No | R$_4$ | R$_5$ | R$_6$ | R$_3$ | Olefin configuration |
|---|---|---|---|---|---|
| 2.001 | OH | H | H | Me | Z |
| 2.002 | OH | H | H | Me | E |
| 2.003 | OEt | H | H | Me | E |
| 2.004 | OEt | H | H | Me | Z |
| 2.005 | OH | 7-Cl | H | Me | E |
| 2.005 | OH | 7-Cl | H | Me | Z |
| 2.007 | OMe | 7-Cl | H | Me | E |
| 2.008 | OMe | 7-Cl | H | Me | Z |
| 2.009 | OH | H | 2-CO$_2$H | Me | Z |
| 2.010 | OEt | 7-Cl | H | Me | Z |
| 2.011 | OH | 7-F | 2-F | Me | Z |
| 2.012 | NH$_2$ | 7-Cl | 2-Cl | Me | Z |
| 2.013 | NHMe | 7-Cl | H | Me | Z |
| 2.014 | SMe | 7-Cl | 2-Cl | Me | Z |

TABLE 2-continued

Compounds of the formula Ib

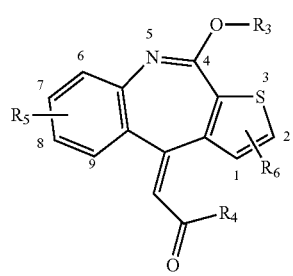

(Ib)

| No | R$_4$ | R$_5$ | R$_6$ | R$_3$ | Olefin configuration |
|---|---|---|---|---|---|
| 2.015 | S(n-propyl) | H | H | Me | Z |
| 2.016 | OH | 7-Cl | 2-Cl | Et | Z |
| 2.017 | OH | 7-Cl | 1-Cl | Me | Z |
| 2.018 | OH | 8-Cl | 2-Cl | Me | Z |
| 2.019 | OEt | 7-Cl | H | Me | E |
| 2.020 | O(n-propyl) | 7-F | H | Et | Z |

TABLE 3

Compounds of the formula Ic

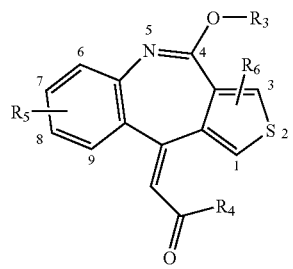

(Ic)

| No | R$_4$ | R$_5$ | R$_6$ | R$_3$ | Olefin configuration |
|---|---|---|---|---|---|
| 3.001 | OH | H | H | Me | E |
| 3.002 | OH | H | H | Me | Z |
| 3.003 | OEt | H | H | Me | E |
| 3.004 | OEt | H | H | Me | Z |
| 3.005 | OH | 7-Cl | H | Me | E |
| 3.006 | OH | 7-Cl | H | Me | Z |
| 3.007 | OMe | 7-Cl | H | Me | E |
| 3.008 | OMe | 7-Cl | H | Me | Z |
| 3.009 | OH | H | 3-CO$_2$H | Me | Z |
| 3.010 | OEt | 7-Cl | H | Me | Z |
| 3.011 | OH | 7-F | 3-F | Me | Z |
| 3.012 | NH$_2$ | 7-Cl | 3-Cl | Me | Z |
| 3.013 | NHMe | 7-Cl | H | Me | Z |
| 3.014 | SMe | 7-Cl | 3-Cl | Me | Z |
| 3.015 | S(n-propyl) | H | H | Me | Z |
| 3.016 | OH | 7-Cl | 3-Cl | Et | Z |
| 3.017 | OH | 7-Cl | 1-Cl | Me | Z |
| 3.018 | OH | 8-Cl | 3-Cl | Me | Z |
| 3.019 | OEt | 7-Cl | H | Me | E |
| 3.020 | O(n-propyl) | 7-F | H | Et | Z |

TABLE 4

Compounds of the formula Id (Id)

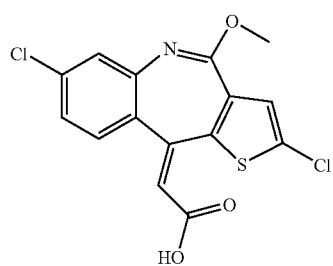

| No | R$_4$ | R$_5$ | R$_6$ | R$_3$ | Olefin configuration |
|---|---|---|---|---|---|
| 4.001 | OH | H | H | Me | Z |
| 4.002 | OH | H | H | Me | E |
| 4.003 | OMe | H | H | Me | Z |
| 4.004 | OEt | H | H | Me | Z |
| 4.005 | OH | 7-Cl | H | Me | E |
| 4.006 | OH | 7-Cl | H | Me | Z |
| 4.007 | OMe | 7-Cl | H | Me | E |
| 4.008 | OMe | 7-Cl | H | Me | Z |
| 4.009 | OH | H | a-CO$_2$H | Me | Z |
| 4.010 | OEt | 7-Cl | H | Me | Z |
| 4.011 | OH | 7-F | a-F | Me | Z |
| 4.012 | NH$_2$ | 7-Cl | c-Cl | Me | Z |
| 4.013 | NHMe | 7-Cl | H | Me | Z |
| 4.014 | SMe | 7-Cl | a-Cl | Me | Z |
| 4.015 | S(n-propyl) | H | H | Me | Z |
| 4.016 | OH | 7-Cl | a-Cl | Et | Z |
| 4.017 | OH | 7-Cl | d-Cl | Me | Z |
| 4.018 | OH | 8-Cl | a-Cl | Me | Z |
| 4.019 | OEt | 7-Cl | H | Me | E |
| 4.020 | O(i-propyl) | 7-F | H | Et | Z |

BIOLOGICAL EXAMPLES

In the following "COMPOUND A" stands for [2,7-Dichloro-10-methoxy-3-thia-9-aza-benzo[f]azulen-(4Z)-ylidene]-acetic acid of the formula

COMPOUND A

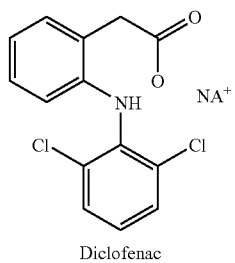

according to preparation example P5.

Diclofenac, derived from benzeneacetic acid, is a NSAID (nonsteroidal anti-inflammatory drug) of cyclooxygenase (COX) inhibitor. This unselective COX-2 inhibitor is used for the treatment of rheumatoid arthritis, osteoarthritis, and ankylosing spondylitis, and also for a variety of non-rheumatic inflammatory conditions. Chemically, it is the sodium salt of 2-[(2,6-dichlorophenyl)amino]benzeneacetic acid showing the following chemical structure:

Diclofenac

Example B1

Effect of COMPOUND A in Dogs with Acute Inflammation of the Stifle Joint (Acute Pain Model/Force Plate Study)

Objective: The objective of this study is to evaluate the analgesic and anti-inflammatory effect of a single dose of COMPOUND A using a model of urate crystal induced synovitis of the stifle joint in dogs via kinetic gait analysis (force plate).

Material and Methods: This trial is performed according a protocol approved by the Novartis Animal Health Research Center in St-Aubin, Switzerland, and in compliance with the Swiss law for animal protection.

Animals: A total of six Beagle dogs (4 males and 2 females) aged between 2 and 9 years and weighing 13 to 15.8 kg are recruited for this study. The dogs are housed in groups of two in light and temperature controlled pens. Each dogs is offered 150-300 g dry pellet food once a day in the morning. Water is available ad libitum through nipple drinkers.

Acute synovitis model: In this study, acute but reversible arthritis is induced by intra-articular (left or right stifle joint) injection of a saline (NaCl 0.9%) suspension containing 15 mg of monosodium urate crystals.

Intra-articular injections: Dogs are sedated with medetomidine (40 microg/kg, i.v.). The left of right stifle joint is clipped and prepared aseptically for intrasynovial injection. A 20-gauge needle is inserted lateral to the patellar ligament and introduced into the articular space. To ensure correct placement of the needle, a small amount of synovial fluid is aspirated with an empty 2 ml syringe. Then, approximately 2 ml of the monosodium urate suspension is injected in the joint cavity through the previously placed needle. Sedation is then antagonized with injection of atipamezol (40 µg/kg, i.v.). Dogs are then brought back to their pens for approximately 3 hours. Usually, after this period, the lameness induced by the injection of the monosodium urate crystals suspension is developed to a point where the dogs become non-weight-bearing on the injected leg during standing, walking and trotting. If at this time the dog's lameness grade is not sufficient, the dogs are excluded from this part of the trial.

Treatments: According to the protocol, both treatments are administered via the oral route approximately 3 hours after the injection of the monosodium urate crystals suspension, and only to the dogs that developed a high-grade lameness. For part 1, half of the dogs are allocated to the COMPOUND A-treated group and the other dogs are allocated to the control group. For part 2, treatments are crossed, so that dogs that are treated with COMPOUND A in part 1 are administered the placebo treatment, and vice versa. The treatments are administered at the doses of 0 mg/kg (placebo) and 2 mg/kg. COMPOUND A is mixed to a placebo formulation (micro-emulsion vehicle without active ingredient) just before administration. The appropriate volumes based on the dogs' bodyweights are given per os with syringes. Thereafter, all syringes are rinsed with NaCl 0.9% and applied to the dogs. The control dogs receive 10 ml of the identical placebo formulation.

Force plate analysis: A biomechanical platform (OR6-6-1000, Advanced Mechanical Technologies Inc., Watertown, Mass.) that measures 3 dimensional forces and impulses is used for our study. The dogs are trotted over the force plate 1, 2, 3, 4 and 6 hours after administration of the treatments to obtain data of vertical forces and impulses of the affected limb. Baseline values included force plate data obtained the day before the induction of lameness and are set as 100% of the dog's capacity. In order to minimize the effect of inter-individual variation we choose to calculate and express the measured data as percentage of the baseline values. By use of a software (Acquire Software 7.20e, Robert Wells, Mich. State University, East Lansing, Mich.) installed with the force plate and a computer, the vertical peak force (ZpkF) is measured. All data are normalized to the bodyweight of the dogs. Data on other ground reaction forces (e.g. vertical impulse, braking and propulsion peak forces) are also recorded and stored but not analyzed. Data from 5 to 6 valid trials of the injected limb at a given measurement time point are averaged and expressed as percentage of the pre-values. If dogs cannot trot over the force plate because they are not bearing enough weight on their injected leg to obtain reliable measures they are given a score of zero, expressing the incapacity of the dog to trot.

Study Design: The study is divided in two parts, each part being identical, with a recovery period of a minimum of 14 days between each part. Each part consists of a force plate analysis trial day. The experimental design is a cross-over design with the advantage that all dogs receive once all treatments (COMPOUND A at 2 mg/kg+placebo) and are their own controls. A recovery period of a minimum of 14 days is shown in previous trials to be sufficient to allow proper healing of the injected stifle joints.

Results: From the twelve planned injections of monosodium urate crystals (6 in each part), 11 induced synovitis as expected, with dogs showing high grade lameness 2 to 3 hours after the injection of monosodium urate crystals. One injection in one dog induced a medium grade lameness; this dog was excluded post-trial. All dogs recovered completely from lameness within 24 hours.

Table 1 shows the results for the injected rear legs of the dogs. The results shown represent mean values of Z-peak force (the maximal vertical force from a leg on the force plate during a step) from the six valid passages of each dog and expressed as percent of the pre-values. Pre-values are measured the day before the induction of lameness. Treatment is given at T=0H. Measures on the force plate are performed pre-treatment (pre-values) and at following time points post-treatment: +1, +2, +3, +4 and +6 hours. The individual results as well as means of the two treatment groups are shown in Table 1.

TABLE 1

Effect of COMPOUND A on lameness in the dog urate crystal synovitis model (H = hour)

| | Placebo treated dogs | | | | | |
|---|---|---|---|---|---|---|
| | 519 | 652 | 664 | 2201 | 2207 | Mean |
| Prevs | 100.0 | 100.0 | 100.0 | 100.0 | 100.0 | 100.0 |
| T + 1 H | 0.0 | 0.0 | 0.0 | 0.0 | 0.0 | 0.0 |
| T + 2 H | 0.0 | 0.0 | 0.0 | 0.0 | 0.0 | 0.0 |
| T + 3 H | 0.0 | 0.0 | 0.0 | 0.0 | 0.0 | 0.0 |
| T + 4 H | 0.0 | 0.0 | 0.0 | 0.0 | 0.0 | 0.0 |
| T + 6 H | 0.0 | 0.0 | 0.0 | 0.0 | 0.0 | 0.0 |
| | COMPOUND A treated dogs | | | | | | |
| | 519 | 525 | 652 | 664 | 2201 | 2207 | Mean |
| Prevs | 100.0 | 100.0 | 100.0 | 100.0 | 100.0 | 100.0 | 100.0 |
| T + 1 H | 0.0 | 0.0 | 0.0 | 0.0 | 0.0 | 0.0 | 0.0 |
| T + 2 H | 0.0 | 65.8 | 0.0 | 0.0 | 0.0 | 0.0 | 11.0 |
| T + 3 H | 86.7 | 93.8 | 71.9 | 79.1 | 0.0 | 0.0 | 55.2 |
| T + 4 H | 87.1 | 103.1 | 82.5 | 58.2 | 80.9 | 0.0 | 68.6 |
| T + 6 H | 106.1 | 106.1 | 87.7 | 85.2 | 83.7 | 78.5 | 91.2 |

Table 1 shows the force plate results of individual dogs (placebo- and COMPOUND A-treated) as well as means of the two treatment groups, i.e. Z peak force (expressed as percent of pre-values) of the injected rear legs of five and six dogs treated with placebo, respectively COMPOUND A.

As seen in Table 1, all dogs are non-weight bearing until time point T+1H. All placebo treated dogs stay lame during the whole post-treatment trial measurement period (0 to 6 hours).

In the group treated with COMPOUND A at 2 mg/kg p.o., one dog shows an early improvement at T+2H; three other dogs show an onset of action at T+3H with Z peak force ranging from 71.9 to 86.7%; the two last dogs responded to the treatment 4 and 6 hours after the administration of COMPOUND A with 80.9 and 78.5% of their pre-values.

The results of this trial demonstrate that the compounds of the formula I, and especially COMPOUND A are promising candidates for the development of pharmaceutical compositions for the treatment of pain and inflammatory effects.

Example B2

Effect of COMPOUND A in a Rat Model of Inflammation and Rheumatoid Arthritis (Carrageenan Edema in the Rat)

Introduction: COMPOUND A is a novel anti-inflammatory drug that inhibits the swelling and histopathological changes in two models of chronic arthritis in rats with very good potency. Additionally, it is active in several models of acute inflammation. The drug is very well tolerated even at doses, which are more than 10 times higher than the effective dose in chronic disease models.

Carrageenan edema in the rat: The effects of COMPOUND A are investigated in the carrageenan edema model. In this model an acute paw swelling is induced by the sub-plantar injection of carrageenan. The paw swelling has a duration of approximately 8 hours and is completely resolved at 24 hours. The model is used to assess anti-inflammatory activities of new therapeutics and is also sensitive to drugs such as COX-inhibitors like Diclofenac, which is used as a positive control compound in the model.

Method: Male OFA rats (5 animals/group) are treated orally with COMPOUND A (1, 3 and 9 mg/kg), Diclofenac (3 mg/kg) or vehicle (placebo formulation). One hour later (0 hours) the rats receive a 100 μl intra-plantar injection of a 1% w/v carrageenan solution in 0.9% saline in the hind paw and the diameter of the paw is measured by means of a micro-caliper. The paw diameter measurements are repeated 3 and 5 hours after injection of the carrageenan. Percentage inhibition of paw swelling at 3 and 5 hours is calculated by reference to vehicle treated animals (0% inhibition).

The effects (% inhibition of swelling) of treatment with COMPOUND A, Diclofenac and vehicle are shown in Table 2.

TABLE 2

Effect of COMPOUND A on paw swelling in the rat carrageenan edema model

|  | Vehicle | COMPOUND A | | | Diclofenac |
|---|---|---|---|---|---|
|  |  | 1 mg/kg | 3 mg/kg | 9 mg/kg | 3 mg/kg |
| 3 hrs | 0% | 58% | 67% | 88% | 91% |
| 5 hrs | 0% | 65% | 48% | 74% | 87% |

Edema is induced by a sub-plantar injection of carrageenan in the paw of the rat. Paw diameters are measured at the time of carrageenan injection (0 hours) and at 3 and 5 hours. Compounds are administered 1 hour before the carrageenan injection. COMPOUND A was dosed at 1, 3 and 9 mg/kg p.o. and Diclofenac at 3 mg/kg p.o.

COMPOUND A demonstrates dose-related inhibition in the carrageenan edema model after 3 and 5 hours, over a dose of 1 to 9 mg/kg. Diclofenac at 3 mg/kg is also very effective in this model with 87-91% inhibition at both times.

The results of this trial demonstrate that the compounds of the formula I, and especially COMPOUND A are promising candidates for the development of pharmaceutical compositions for the treatment of arthritis.

Example B3

Collagen-Induced Arthritis (Cartilage Protection, Disease Modification, Prophylactic Treatment)

Animal models of RA need to reflect at least some of the features found in human RA (Billingham et al., 1979). Collagen-induced arthritis (CIA) has been proposed to meet these requirements (Durie et al., 1994). Especially the similarity in the joint pathophysiology makes this animal model most attractive for the evaluation of anti-rheumatic drugs (Takeshita et al., 1997). Synovial hyperplasia, which is an integral part of the disease, parallels the migration of leukocytes into the joint space; erosion and destruction of the cartilage surface can also be found (Holmdahl et al., 1985). The rat CIA, originally described by Trentham et al. (1977), was established and extensive studies with CsA were done, including three-dimensional magnetic resonance imaging (MRI) and histology (Beckmann et al., 1995; 1998). Differences in the susceptibility of several rat strains for the development of the disease have been reported (Cremer et al., 1995; Kamada et al., 1997; Knoerzer et al., 1997).

Method: For this study, COMPOUND A and COX-inhibitor Diclofenac are dissolved in a solvent containing 5% of glucose (5 ml/kg). Compounds are given orally once a day. Female rats of the WAGxBUF/F1 crossbred strain (weight 130 g) are used. The animals are divided into several groups, one placebo group (N=8), and four treatment groups (each N=7-8). Treatment starts on peak of disease (day 0) and continues for 11 days. Swelling is assessed at regular time intervals by measuring the external thickness of the hind paws in the region of the metatarsals using a micro-caliper. Tissue samples for histological evaluation are obtained at the end of the in vivo experiment, 5 h after the last oral dose of COMPOUND A or placebo on day 11.

Results:

Swelling of Hind Paws:

Mean diameter of the hind paws of the rats before immunization is 3.09±0.01 mm and increased up to 5.36±0.14 mm immediately before treatment with COMPOUND A or Diclofenac (day 0). From day 0 to day 11, the swelling of the hind paws of animals treated with vehicle, COMPOUND A or Diclofenac decreases (Table 3).

TABLE 3

Means of groups treated with COMPOUND A and Diclofenac of hind paw swelling in the collagen-induced arthritis in the rats

|  | Vehicle n = 8 | COMPOUND A | | | | Diclofenac 1 mg/kg n = 4 |
|---|---|---|---|---|---|---|
|  |  | 0.3 mg/kg n = 8 | 1 mg/kg n = 7 | 3 mg/kg n = 7 | 9 mg/kg n = 7 |  |
| Day −12 | 3.119 ± 0.023 | 3.069 ± 0.016 | 3.107 ± 0.046 | 3.136 ± 0.026 | 3.043 ± 0.028 | 3.038 ± 0.024 |
| Day 0 | 5.356 ± 0.446 | 5.406 ± 0.448 | 5.350 ± 0.344 | 5.379 ± 0.224 | 5.364 ± 0.231 | 5.300 ± 0.265 |
| Day 11 | 4.742 ± 0.161 | 4.417 ± 0.079 | 3.983 ± 0.064 | 3.592 ± 0.085 | 3.275 ± 0.038 | 3.750 ± 0.029 |

Results shown are means±SEM of groups of each 4-8 animals of paw diameters in mm on day-12 (before the immunization with Type II collagen in incomplete Freund's adjuvant), day 0 (start of treatment) and day 11 (end of treatment).

The effect of COMPOUND A on the paw swelling is shown in Table 4. The data shown represent the ability of the treatment (COMPOUND A at 4 different increasing doses) to reduce the volume of the hind paw measured at day 2, day 7 and day 11.

TABLE 4

Effect of COMPOUND A on hind paw swelling in the collagen-induced arthritis in the rats

|  | COMPOUND A | | | |
|---|---|---|---|---|
|  | 0.3 mg/kg n = 8 | 1 mg/kg n = 7 | 3 mg/kg n = 7 | 9 mg/kg n = 7 |
| Day 2 | −33% ** | −40% ** | −59% *** | −69% *** |
| Day 7 | −31% * | −38% ** | −47% *** | −75% *** |
| Day 11 | −20% | −47% *** | −71% *** | −90% *** |
| Day 0-11 | −29 ± 9.2% | −37 ± 6.8% | −51 ± 7.1% | −67 ± 5.4% |

Dunnett 2-sided Test:
* $p < 0.05$,
** $p < 0.01$,
*** $p < 0.001$, other values not significant COMPOUND A given at doses of 0.3, 1, 3 and 9 mg/kg per day p.o., rapidly, dose-dependently and statistically significantly decreases the hind paw swelling (from day 2 to 11). An analysis of the AUC during day 0 to 11 reveals median inhibitions of swelling of 29±9.2% (at 0.3 mg/kg), 37±6.8% (at 1 mg/kg), 51±7.1% (at 3 mg/kg) and 67±5.4% (at 9 mg/kg), respectively. Diclofenac inhibits the paw swelling to a significant extent (57±9.9%) when this compound is given at a dose of 1 mg/kg per day p.o. A detrimental effect on body weight gain is not observed with COMPOUND A.

Histology:

Hind paws from control arthritic rats (vehicle-treated), taken post-mortem at the end of day 11 of the treatment, obtained relatively high histological scorings compared to histological scores of animals treated with COMPOUND A (0.3, 1, 3 and 9 mg/kg) or Diclofenac (1 mg/kg).

TABLE 5

Effect of COMPOUND A and Diclofenac on four histological parameters in the collagen-induced arthritis in the rats

|  | COMPOUND A | | | | Diclofenac |
|---|---|---|---|---|---|
|  | 0.3 mg/kg | 1 mg/kg | 3 mg/kg | 9 mg/kg | 1 mg/kg |
| Bone apposition | +4% | −28% | −35% * | −51% ** | −38% |
| Loss of PG | +1% | −13% | −28% * | −40% * | −24% |
| Cartilage damage | −6% | −24% | −40% * | −56% *** | −32% |
| Infiltration of cells | +8% | −7% | −25% | −34% ** | −22% |

* $p < 0.05$,
** $p < 0.01$,
*** $p < 0.001$ (Mann-Whitney-Wilcoxon rank sum test)

COMPOUND A (at doses of 0.3 to 9 mg/kg/day) reduced the scores of the four parameters dose-dependently with very significant effects at the highest dose ($p \leq 0.01$), thus clearly demonstrating the protective effects of this compound on the erosive and tissue proliferating processes within the affected joints.

Conclusion: COMPOUND A very significantly and dose-dependently decreases the swelling of hind paws already as soon as day 2 of treatment, an effect that is even stronger by days 7 to 11 of the therapy. In this respect, the compound is quite comparable to an active reference compound such as the COX-inhibitor Diclofenac. COMPOUND A does not interfere with body weight gain, which would indicate adverse or toxic effects. Moreover, the general behavior of all animals is normal.

Histological evaluation of four parameters investigated in the hind paws of the rats at the end of the study also clearly demonstrates therapeutic efficacy, showing protective effects of COMPOUND A in a dose-dependent fashion on the erosive and tissue proliferating processes within the affected joints.

The results of this trial demonstrate that the compounds of the formula I, and especially COMPOUND A show a significant therapeutic effect on erosive and tissue proliferating processes within the affected joints. They are promising candidates for the development of pharmaceutical compositions for the treatment of anti-inflammatory pharmaceutical compositions.

Example B4

Adjuvant-Induced Arthritis/Chronic Inflammation

Adjuvant arthritis in the rat has been the most frequently used model of chronic inflammation. It is also one of the most commonly used models for evaluating anti-inflammatory and anti-arthritic drugs (Billingham, 1983). A chronic polyarthritis develops in several joints after the intradermal injection of complete Freund's adjuvant (Winter and Nuss, 1966). The lesions are characterized by swelling, periostitis and bone remodeling. The lesion is predominantly a periarthritis rather than a true arthritis. Any cartilage destruction which does occur seems to be secondary to bone resorption and there is no evidence of a direct attack on cartilage as an initiating event (Smith et al., 1982).

Adjuvant arthritis can be treated using two different dosing schedules; either starting at the time of immunization with adjuvant (prophylactic dosing) or from day 15 when the arthritic response is already established (therapeutic dosing). It is more difficult to inhibit adjuvant arthritis with the therapeutic dosing schedule as compared to the prophylactic schedule. Both versions of adjuvant arthritis are, however, extremely sensitive to the effects of both non-selective COX inhibitors and COX 2 selective inhibitors where 70-90% inhibition of swelling can be achieved at appropriate doses. These models may be predictive for some of the processes thought to be relevant in rheumatoid arthritis.

Arthritis Induction:

Method: Female Wistar rats weighing 150-170 g (housed in standard conditions, 5 animals per cage, with food and water ad libitum) are injected i.d. at the base of the tail with 0.1 ml of mineral oil containing 0.6 mg of lyophilized heat-killed *Mycobacterium tuberculosis*. The rats are treated orally with COMPOUND A or placebo formulation from day 15 to day 22 (therapeutic dosing schedule) or with COMPOUND A from day 0 to day 14 after immunization (prophylactic dosing schedule). At the end of the experiment, the swelling of the tarsal joints is measured by means of a micro-caliper. For the comparison study to Diclofenac both compounds are given from day 15 to day 29 with readouts at day 22 and 29. Percentage inhibition of paw swelling is calculated by reference to placebo treated arthritic animals (0% inhibition) and placebo treated normal animals (100% inhibition). Five animals are used per group. Data are analyzed using Kruskal-Wallis non-parametric ANOVA followed by Dunn's Multiple Comparison test.

Results:

TABLE 6

Comparison of the effects of different doses of COMPOUND A in the developing Adjuvant-induced arthritis in rats (prophylactic dosing schedule)

| Compound | Dose mg/kg | Swelling (mm) ± SEM | % inhibition |
|---|---|---|---|
| Arthritic Controls day 0 | — | 7.3 ± 0.2 | — |
| Arthritic Controls day 14 | 5 ml/kg | 11.5 ± 0.7 | — |
| COMPOUND A | 0.3 | 10.9 ± 0.6 | 14.3 * |
|  | 1 | 9.1 ± 0.5 | 57.1 * |
|  | 3 | 7.8 ± 0.2 | 88.1 ** |

* n.s.
** $p < 0.05$ (compared to arthritic control animals).

COMPOUND A at dose of 3 mg/kg p.o. inhibits the development of swelling in the developing adjuvant-induced arthritis by 88%. The calculated $ED_{50}$ is 0.8 mg/kg p.o.

TABLE 7

Comparison of the effects of different doses of COMPOUND A in the established Adjuvant-induced arthritis in rats (therapeutic dosing schedule)

| Compound | Dose mg/kg | Swelling (mm) ± S.D. | % inhibition |
|---|---|---|---|
| Arthritic Controls | 5 ml/kg | 8.06 ± 1.01 | — |
| Diclofenac | 1 | 4.27 ± 0.31 | 47.1 * |
| COMPOUND A | 0.3 | 6.79 ± 0.9 | 15.8 * |
|  | 1 | 4.92 ± 0.63 | 39.0 * |
|  | 3 | 4.41 ± 0.59 | 45.0 * |
|  | 9 | 2.84 ± 0.73 | 64.7 ** |

* n.s.
** $p < 0.001$ (compared to arthritic control animals, 7 day treatment)

COMPOUND A given at 9 mg/kg/day inhibits the swelling of hind paws in the established adjuvant-induced arthritis with a maximum inhibition of about 65%. In comparison, Diclofenac (1 mg/kg/day) inhibits the swelling by up to 47%.

TABLE 8

Comparison of the effects of COMPOUND A in the established Adjuvant-induced arthritis in rats after a one or two week treatment schedule

| Compound | Dose mg/kg | Swelling (mm) ± S.D. 7 days treatment | % inhibition | Swelling (mm) ± S.D. 14 days treatment | % inhibition |
|---|---|---|---|---|---|
| Arthritic Controls | 5 ml/kg | 8.62 ± 0.69 | — | 7.70 ± 1.12 | — |
| COMPOUND A | 1.25 | 4.22 ± 0.57 | 51.0 * | 3.06 ± 0.63 | 60.3 * |
|  | 2.5 | 3.40 ± 0.92 | 60.5 * | 2.93 ± 0.80 | 62.0 * |
|  | 5 | 2.94 ± 1.28 | 65.0 * | 2.23 ± 0.66 | 71.1 * |

* $p < 0.01$ (compared to arthritic control animals, readouts at day 22 and day 29).

COMPOUND A inhibits the swelling of hind feet in the established adjuvant-induced arthritis with a maximum inhibition of about 71% (COMPOUND A at 5 mg/kg/day) after 14 days of treatment. Estimated $ED_{50}$'s for COMPOUND A are equal or less than 1.25 mg/kg p.o. using a one week treatment schedule and less than 1.25 when using a 2 week treatment schedule.

What is claimed is:

1. A compound of the formula Ia

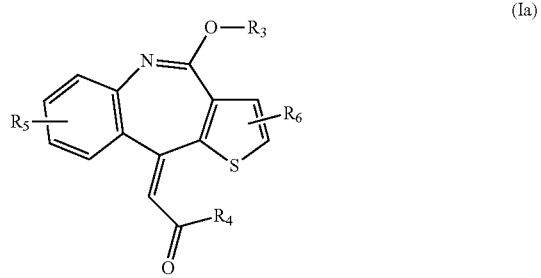

(Ia)

wherein $R_3$ is $C_1$-$C_6$-alkyl;

$R_4$ is OH, $NH_2$, or $C_1$-$C_6$-alkyloxy;

$R_5$ is H, or halogen; and $R_6$ is H, halogen, $NO_2$, CN or $C_1$-$C_6$-alkyl;

or a physiologically acceptable ester or a pharmaceutical acceptable salt thereof.

2. A compound of formula Ia according to claim 1, wherein $R_3$ is methyl or ethyl; and $R_4$ is OH, methoxy or ethoxy.

3. A compound according to claim 1 selected from the group consisting of [7-Chloro-10-hydroxy-3-thia-9-aza-benzo[f]azulen-4-ylidene]-acetic acid; [7-Chloro-10-methoxy-3-thia-9-aza-benzo[f]azulen-4-ylidene]-acetic acid; [7-Chloro-10-ethoxy-3-thia-9-aza-benzo[f]azulen-4-ylidene]-acetic acid; [2-Chloro-10-hydroxy-3-thia-9-aza-benzo[f]azulen-4-ylidene]-acetic acid; [2-Chloro-10-methoxy-3-thia-9-aza-benzo[f]azulen-4-ylidene]-acetic acid; [2-Chloro-10-ethoxy-3-thia-9-aza-benzo[f]azulen-4-ylidene]-acetic acid; [2-Chloro-7-fluoro-10-hydroxy-3-thia-9-aza-benzo[f]azulen-4-ylidene]-acetic acid; (2-Chloro-7-fluoro-10-methoxy-3-thia-9-aza-benzo[f]azulen-4-ylidene]-acetic acid; [2-Chloro-7-fluoro-10-ethoxy-3-thia-9-aza-benzo[f]azulen-4-ylidene]-acetic acid; [2,7-Difluoro-10-hydroxy-3-thia-9-aza-benzo[f]azulen-4-ylidene]-acetic acid; [2,7-Difluoro-10-methoxy-3-thia-9-aza-benzo[f]azulen-4-ylidene]-acetic acid; [2,7-Difluoro-10-ethoxy-3-thia-9-aza-benzo[f]azulen-4-ylidene]-acetic acid; [2,7-Dichloro-10-hydroxy-3-thia-9-aza-benzo[f]azulen-4-ylidene]-acetic acid; [2,7-Dichloro-10-ethoxy-3-thia-9-aza-benzo[f]azulen-4-ylidene]-acetic acid; and [2,7-Dichloro-10-methoxy-3-thia-9-aza-benzo[f]azulen-4-ylidene]-acetic acid or a physiologically acceptable ester or a pharmaceutically acceptable salt thereof.

4. A compound according to claim 3, wherein the compound is cis[2,7-Dichloro-10-methoxy-3-thia-9-aza-benzo[f]azulen-4-ylidene]-acetic acid or a physiologically acceptable ester or a pharmaceutically acceptable salt thereof.

5. A pharmaceutical composition comprising a therapeutically effective amount of a compound according to claim 1 and a physiologically acceptable adjuvant, diluent or carrier.

6. The pharmaceutical composition according to claim 5, wherein said composition is an oral or transdermal dosage form.

7. The pharmaceutical composition according to claim 5 wherein said composition is a veterinary composition in a palatable dosage form.

8. A method of treating pain or discomfort of inflammatory ailments in a human or animal in need of such treatment, which method comprises administering to said subject an analgesically effective amount of a compound according to claim 1.

9. A compound according to claim 3, wherein the compound is [2,7-Dichloro-10-methoxy-3-thia-9-aza-benzo[f]azulen-4-ylidene]-acetic acid.

10. A pharmaceutical composition comprising the compound of claim 9 and a physiologically acceptable adjuvant, diluent, or carrier.

11. A method of treating pain in a subject in need thereof, comprising administering the compound of claim 9.

12. A process for preparing a compound of formula Ia according to claim 1, wherein a compound of formula

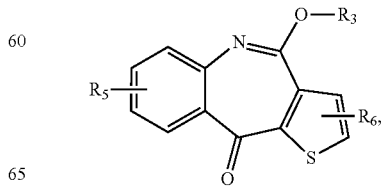

VI wherein $R_3$, $R_5$ and $R_6$ are defined as given for formula Ia, is reacted with a compound of formula (MeO)$_2$POCH$_2$COOMe    IX, optionally in the presence of a basic catalyst to form a compound of formula Ia.

13. The process of claim 12, wherein said compound of formula Ia is a racemic ester, the process further comprising the step of saponifying said ester and isolating at least one isomer of said compound.

14. A compound of formula Ia according to claim 1, wherein $R_3$ is $C_1$-$C_6$-alkyl, $R_4$ is OH, NH$_2$ or $C_1$-$C_6$-alkyloxy, $R_5$ is halogen, and $R_6$ is H or halogen, or a pharmaceutically acceptable salt thereof.

15. A compound of the formula I according to claim 14, wherein $R_3$ is methyl or ethyl.

* * * * *